US009714206B2

(12) United States Patent
Vetter et al.

(10) Patent No.: US 9,714,206 B2
(45) Date of Patent: Jul. 25, 2017

(54) METHYL-IODIDE-FREE CARBONYLATION OF AN ALCOHOL TO ITS HOMOLOGOUS ALDEHYDE AND/OR ALCOHOL

(71) Applicant: Eastman Chemical Company, Kingsport, TN (US)

(72) Inventors: Andrew James Vetter, Kingsport, TN (US); Jonathan Michael Penney, Gray, TN (US); David William Norman, Cary, NC (US)

(73) Assignee: Eastman Chemical Company, Kingsport, TN (US)

( * ) Notice: Subject to any disclaimer, the term of this patent is extended or adjusted under 35 U.S.C. 154(b) by 27 days.

(21) Appl. No.: 14/585,915

(22) Filed: Dec. 30, 2014

(65) Prior Publication Data

US 2016/0185701 A1   Jun. 30, 2016

(51) Int. Cl.
| | |
|---|---|
| C07C 45/00 | (2006.01) |
| C07C 45/49 | (2006.01) |
| B01J 31/24 | (2006.01) |
| C07C 29/16 | (2006.01) |
| C07C 45/50 | (2006.01) |
| C07C 51/12 | (2006.01) |

(52) U.S. Cl.
CPC ......... *C07C 45/49* (2013.01); *B01J 31/2409* (2013.01); *C07C 29/16* (2013.01); *C07C 45/50* (2013.01); *C07C 51/12* (2013.01); *B01J 2231/34* (2013.01); *B01J 2531/845* (2013.01)

(58) Field of Classification Search
None
See application file for complete search history.

(56) References Cited

U.S. PATENT DOCUMENTS

| | | | |
|---|---|---|---|
| 2,727,902 | A | 12/1955 | Reppe |
| 4,239,705 | A | 12/1980 | Pretzer et al. |
| 4,293,718 | A | 10/1981 | Gauthier-Lafaye et al. |
| 4,306,091 | A | 12/1981 | Gauthier-Lafaye et al. |
| 4,361,706 | A | 11/1982 | Habib et al. |
| 4,374,285 | A | 2/1983 | Lin et al. |
| 4,374,752 | A | 2/1983 | Argento et al. |
| 4,389,532 | A | 6/1983 | Larkins, Jr. et al. |
| 4,400,551 | A | 8/1983 | Keim et al. |
| 4,484,002 | A | 11/1984 | Lin |
| 4,556,744 | A | 12/1985 | Griggs et al. |
| 4,954,665 | A | 9/1990 | Vidal |
| 5,770,541 | A | 6/1998 | Vanderspurt et al. |
| 5,908,807 | A | 6/1999 | Vanderspurt et al. |
| 5,939,352 | A | 8/1999 | Vanderspurt et al. |
| 6,034,141 | A | 3/2000 | Vanderspurt et al. |
| 7,700,192 | B2 | 4/2010 | Matthews et al. |
| 7,700,813 | B2 | 4/2010 | Kourtakis et al. |
| 7,745,672 | B2 | 6/2010 | Kourtakis et al. |
| 8,304,587 | B2 | 11/2012 | Warner et al. |
| 2007/0293695 | A1 | 12/2007 | Zoeller et al. |
| 2009/0247783 | A1 | 10/2009 | Zoeller et al. |

FOREIGN PATENT DOCUMENTS

| | | |
|---|---|---|
| CN | 101703926 A | 5/2010 |
| DE | 33 43 519 A1 | 6/1985 |
| DE | 35 06 714 A1 | 8/1986 |
| EP | 0 037 586 A1 | 10/1981 |
| FR | 697 726 | 1/1931 |
| FR | 697 727 | 1/1931 |
| FR | 697 896 | 1/1931 |
| JP | 2000 172854 A | 6/2000 |

OTHER PUBLICATIONS

Cu Igai, Liu, et al.; "Effect of Double Promoters on CuO/SiO$_2$ Catalyst for Synthesis of Isobutyraldehyde from Methanol and Ethanol"; Petrochemical Technology; pp. 550-553; 2011 (original language and English abstract).
Wang, Fey-Long, et al.; "Alkylation of aldehydes with methanol over titanium oxide catalysts"; Catalysis Letters, vol. 42; pp. 155-160; 1996.
Notice of Allowance dated Sep. 18, 2015 received in U.S. Appl. No. 14/586,094.
Notice of Allowance dated Sep. 29, 2015 received in U.S. Appl. No. 14/585,940.
Bahrmann, Helmu; "Homologation—3.2 Special Catalysts and Processes"; Applied Homogeneous Catalysis Organometallic Compounds, vol. 2; pp. 902-914; 1996.
Dinka, P. et al.; "Reaction of methanol and n-propanol over hydrotalcite-like catalysts containing vanadium oxide"; Applied Clay Science, vol. 13; pp. 467-477; 1998.
Gauthier-Lafaye, Jean and Perron, Robert; "Chapter 4 Synthesis of acetaldehyde and ethanol"; methanol and carbonylation; pp. 39-96; 1987.
Gauthier-Lafaye, J. et al.; "Methanol Hydrocarbonylation into Acetaldehyde Catalyzed by Cobalt and Two Different Iodides"; Journal of Molecular Catalysis, vol. 17; pp. 339-347; 1982.
Girard, James W. et al.; "Technical Advantages of Vandium SCR Systems for Diesel NOx Control in Emerging Markets"; SAE Int. J. Fuels Lubr, vol. 1, Issue 1; pp. 488-494; 2008.
Hong, H. et al.; "Study of V$_2$ O$_5$ Catalyst Deactivation for the Synthesis of Isobutyraldehyde from Methanol and Ethanol"; Chemical Engineering of Oil & Gas, vol. 37, No. 1; pp. 5-8; Feb. 2008 (original language and English abstract).
Hong, H. et al.; "Macrokinetics of Synthesis of Isobutyraldehyde from Methanol and Ethanol over V$_2$O$_5$ Catalyst"; Chemical Engineering of Oil & Gas, vol. 37, No. 5, pp. 370-372; Oct. 2008 (original language and English abstract).

(Continued)

*Primary Examiner* — Fereydoun G Sajjadi
*Assistant Examiner* — Ana Z Muresan

(57) ABSTRACT

Disclosed is a process for the reductive carbonylation of a low molecular weight alcohol to produce the homologous aldehyde and/or alcohol. The process includes conducting the reaction to produce the aldehyde in the presence of a catalyst complex composed of cobalt, an onium cation and iodide in a ratio of 1:2:4 with a phosphine ligand. A ruthenium co-catalyst is used in the production of the homologous alcohol. The reductive carbonylation reaction does not require an additional iodide promoter and produces a crude reductive carbonylation product substantially free of methyl iodide.

34 Claims, No Drawings

(56) References Cited

OTHER PUBLICATIONS

Keim, W.; "Carbon monoxide: feedstock for chemicals, present and future"; Journal of Organometallic Chemistry, vol. 372; pp. 15-23; 1989.

Loevenich, Heinz and Röper, Michael; "Kinetic Studies of Methanol Homologation Using Cobalt-Phosphine-Iodine Catalysts"; $C_1$ Molecular Chemistry, vol. 1; pp. 155-170; 1984.

Mizoroki, Tsutomu et al.; "Further Study of Methanol Carbonylation Catalyzed by Cobalt, Rhodium, and Iridium Catalysts"; Bulletin of the Chemical Society of Japan, vol. 52, No. 2; pp. 479-482; 1979.

Moloy, Kenneth G. and Wegman, Richard W.; "Rhodium-Catalyzed Reductive Carbonylation of Methanol"; Organometallics, vol. 8; pp. 2883-2892; 1989.

Reddy, B. Mahipal et al.; "A Single-Step Synthesis of Isobutyraldehyde from Methanol and Ethanol over CuO—ZnO—$Al_2O_3$ Catalyst"; Journal Chemical Society, Chemical Commun.; pp. 997-998; 1992.

Reddy, B. M. et al.; "Vapour Phase Synthesis of Isobutyraldehyde from Methanol and Ethanol over Mixed Oxide Supported Vanadium Oxide Catalysts"; Res. Chem. Intermed., vol. 23, No. 8; pp. 703-713; 1997.

Sharutin, V. V. et al.; "Synthesis and Structure of Cobalt Complexes $[Me_3EtN]+_2[CoI_4]^{-2-}$ and $[Me_3BuN]+_2[CoI_4]^{-2-}$"; Russian Journal of Inorganic Chemistry, vol. 56, No. 9; pp. 1384-1389; 2011.

Twigg, Martyn V.; "Progress and future challenges in controlling automotive exhaust gas emissions"; Applied Catalysis B: Environmental, vol. 70; pp. 2-15; 2007.

Wang, Fey-Long and Lin, Yi-Hsuan; "Alkylation of Acetaldehyde with Methanol over Titanium Oxide-Supported Vanadium Oxide"; Chemistry Letters; pp. 1867-1868; 1992.

Wang, Hui-Ying, et al.; "$V_2O_5$/$TiO_2$-$SiO_2$ Catalysts for the Synthesis of Isobutyraldehyde from Methanol and Ethanol"; Journal of Shenyang Institute of Chemical Technology, vol. 22, No. 3; pp. 200-203; Sep. 2008 (original language and English abstract).

Wender, Irving et al.; "Ethanol from Methanol"; Science, vol. 113; pp. 206-207; Feb. 23, 1951.

Wegman, Richard W. and Busby, David C.; "The Role of Phosphines and Solvents in $CoI_2$-Catalyzed Reductive Carbonylation of Methanol"; Journal of Molecular Catalysis, vol. 32; pp. 125-136; 1985.

Co-pending U.S. Appl. No. 14/585,884, filed Dec. 30, 2014; Penny et al.

Notice of Allowance dated Jun. 10, 2015 received in U.S. Appl. No. 14/585,884.

Co-pending U.S. Appl. No. 14/586,070, filed Dec. 30, 2014; Vetter et al.

Non-Final Office Action dated Jun. 9, 2015 received in U.S. Appl. No. 14/586,070.

Co-pending U.S. Appl. No. 14/586,094, filed Dec. 30, 2014; Norman et al.

Notice of Allowance dated Jun. 11, 2015 received in U.S. Appl. No. 14/586,094.

Co-pending U.S. Appl. No. 14/585,940, filed Dec. 30, 2014; Penny et al.

Non-Final Office Action dated Jun. 9, 2015 received in U.S. Appl. No. 14/585,940.

Notice of Allowance dated Nov. 12, 2015 issued in U.S. Appl. No. 14/586,070.

Office Communication dated Feb. 26, 2016 issued in U.S. Appl. No. 14/585,884.

Notice of Allowance dated Apr. 26, 2016 issued in U.S. Appl. No. 14/585,884.

METHYL-IODIDE-FREE CARBONYLATION OF AN ALCOHOL TO ITS HOMOLOGOUS ALDEHYDE AND/OR ALCOHOL

FIELD OF THE INVENTION

This invention relates to a process for the reductive carbonylation of a low molecular weight alcohol to produce the homologous aldehyde and/or alcohol. For example, this invention relates to a process for the reductive carbonylation of methanol, hydrogen, and carbon monoxide to form acetaldehyde, and/or ethanol. The invention relates to the reductive carbonylation of a low molecular weight alcohol without the need to use methyl iodide as a co-catalyst. Specifically the invention relates to a process of conducting the reductive carbonylation reaction in the presence of a catalyst composition comprising a complex composed of cobalt, an onium cation, and iodide, and a phosphine ligand such that there is less than one weight percent methyl iodide in the crude reductive carbonylation product.

BACKGROUND OF THE INVENTION

Cobalt can catalyze the formation of acetaldehyde from methanol, carbon monoxide, and hydrogen, a reaction known as methanol reductive carbonylation. For example, it was disclosed by Wender et al., *Science*, 113, (1951), 206-207, that a cobalt carbonyl catalyst system could be used. However, the product of the disclosed process was primarily ethanol, together with a small amount of acetaldehyde. It was later shown that the addition of iodide to a cobalt-containing catalyst system increased the amount of acetaldehyde produced. Iodide is typically added as a co-catalyst (also commonly referred to as a promoter) to the reaction in a form such as hydrogen iodide (a strong acid), methyl iodide, elemental iodide, or as an iodide salt such as lithium iodide or sodium iodide.

Homologation of methanol to ethanol can be achieved by addition of a hydrogenation catalyst, typically ruthenium based, to a reductive carbonylation system. For example, Mizoroki, et al., *Bull. Chem. Soc. Japan*, 52, (1979), 479-482, have described a catalyst system containing a cobalt compound, a ruthenium compound and methyl iodide to convert methanol to ethanol with 77% selectivity.

Addition of iodide co-catalysts in these reactions often leads to formation of dimethyl ether as well as free methyl iodide in the crude reductive carbonylation product. Methyl iodide is an undesirable co-product due to the difficulty in separating it from the aldehyde and/or alcohol product as well as its toxicity. Current methanol reductive carbonylation processes carefully balance the amount of iodide containing compounds added to the reaction to obtain optimized reaction rate and conversion while limiting dimethyl ether and methyl iodide formation.

There is a need for an improved catalyst system which will allow reasonable reductive carbonylation reaction rates as well as little to no methyl iodide in the crude reductive carbonylation product. Additionally there is a need to readily influence the relative amounts of aldehyde and/or alcohol produced in a reductive carbonylation reaction to maximize the desired product profile.

There is also a need for an inexpensive catalyst for the reductive carbonylation of alcohol that can replace the typical rhodium catalyst or iridium/ruthenium catalyst while producing a substantially methyl iodide free crude reductive carbonylation product.

SUMMARY OF THE INVENTION

The present invention provides in a first embodiment a catalyst composition comprising a complex of cobalt, iodide, and an onium cation or an alkali metal cation of the general formula $Y_2CoI_4$. Y is the onium cation or alkali metal cation. The catalyst composition also comprises a phosphine ligand of the general formula

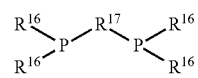

The phosphorus atoms P are bridged by 2 to 6 atoms of $R^{17}$. $R^{17}$ is selected from the group consisting of a substituted or unsubstituted alkylene, cycloalkylene, arylene, and biarylene, each having up to 22 carbon atoms. A heteroatom, optionally, can substitute for one or more of the carbon atoms. The heteroatom can be nitrogen, oxygen, sulfur, phosphorus or mixtures thereof. $R^{16}$ can be substituted or unsubstituted alkyl, alkoxy, cycloalkyl, aryl, or aryloxy, each having up to 20 carbon atoms.

The present invention provides in a second embodiment a process for the preparation of a crude reductive carbonylation product comprising contacting hydrogen, carbon monoxide, and an alcohol having 1 to 3 carbon atoms in the presence of a catalyst composition to form the crude reductive carbonylation product. The crude reductive carbonylation product comprises homologous aldehyde equivalents in a higher mole percent than homologous acid equivalents or homologous alcohol equivalents, each based on the total moles of the homologous aldehyde equivalents, the homologous acid equivalents, and the homologous alcohol equivalents. The catalyst composition comprises a complex of cobalt, iodide, and an onium cation or an alkali metal cation of the general formula $Y_2CoI_4$, where Y represents the onium cation or the alkali metal cation. The catalyst composition also comprises a phosphine ligand of the general formula

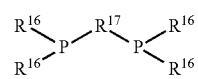

The phosphorus atoms P are bridged by 2 to 6 atoms of $R^{17}$. $R^{17}$ is selected from the group consisting of a substituted or unsubstituted alkylene, cycloalkylene, arylene, and biarylene, each having up to 22 carbon atoms. A heteroatom, optionally, can substitute for one or more of the carbon atoms. The heteroatom can be nitrogen, oxygen, sulfur, phosphorus or mixtures thereof. $R^{16}$ can be substituted or unsubstituted alkyl, alkoxy, cycloalkyl, aryl, or aryloxy, each having up to 20 carbon atoms. The crude reductive carbonylation product comprises less than 1 weight percent of methyl iodide.

The present invention provides in a third embodiment a process for the preparation of a crude reductive carbonylation product comprising contacting hydrogen, carbon monoxide, and methanol in the presence of a catalyst composition to form the crude reductive carbonylation product. The crude reductive carbonylation product comprises acetaldehyde equivalents in a higher mole percent than acetic acid equivalents or ethanol equivalents, each based on the total moles of the acetaldehyde equivalents, the acetic acid equivalents, and the ethanol equivalents. The catalyst composition comprises a complex of cobalt, iodide, and an onium cation of the general formula $Y_2CoI_4$, where Y represents the onium cation. The onium cation is of the general formula (I) or (II)

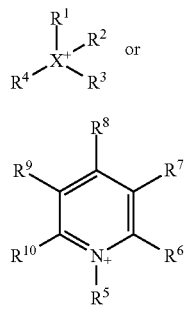

For formula (I), X is phosphorus (P) and $R^1$ is methyl. $R^2$, $R^3$, and $R^4$ are independently selected from alkyl having up to 12 carbons and aryl. When $R^2$, $R^3$, and/or $R^4$ are aryl, each aryl is the same, and can be phenyl, tolyl, xylyl, or mesityl. For formula (II), $R^5$ is methyl and $R^6$, $R^7$, $R^8$, $R^9$, and $R^{10}$ are hydrogen. The catalyst composition also comprises a phosphine ligand. The phosphine ligand can be 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1-tris(diphenylphosphinomethyl)ethane; 1,1,1-tris(diethylphosphinomethyl)ethane; 1,3-bis(dicyclohexylphosphino)propane; 1,3-bis(dimethylphosphino)propane; 1,3-bis(diisopropylphosphino)propane; 1,3-bis(di-tert-butylphosphino)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; or 1,3-bis(diphenylphosphino)cyclobutane. The crude reductive carbonylation product comprises less than 1 weight percent of methyl iodide.

The present invention provides in a fourth embodiment a process for the preparation of a crude reductive carbonylation product comprising contacting hydrogen, carbon monoxide, and an alcohol having 1 to 3 carbon atoms in the presence of a catalyst composition to form the crude reductive carbonylation product. The crude reductive carbonylation product comprises homologous alcohol equivalents in a higher mole percent than homologous aldehyde equivalents or homologous acid equivalents, each based on the total moles of the homologous aldehyde equivalents, the homologous acid equivalents, and the homologous alcohol equivalents. The catalyst composition comprises a complex of cobalt, iodide, and an onium cation or an alkali metal cation of the general formula $Y_2CoI_4$, where Y represents the onium cation or the alkali metal cation. The catalyst composition also comprises a phosphine ligand of the general formula

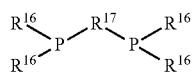

The phosphorus atoms P are bridged by 2 to 6 atoms of $R^{17}$. $R^{17}$ is selected from the group consisting of a substituted or unsubstituted alkylene, cycloalkylene, arylene, and biarylene, each having up to 22 carbon atoms. A heteroatom, optionally, can substitute for one or more of the carbon atoms. The heteroatom can be nitrogen, oxygen, sulfur, phosphorus or mixtures thereof. $R^{16}$ can be substituted or unsubstituted alkyl, alkoxy, cycloalkyl, aryl, or aryloxy, each having up to 20 carbon atoms. The process further comprises a ruthenium co-catalyst. The crude reductive carbonylation product comprises less than 1 weight percent of methyl iodide.

DETAILED DESCRIPTION

The present invention provides in a first embodiment a catalyst composition comprising a complex of cobalt, iodide, and an onium cation or an alkali metal cation of the general formula $Y_2CoI_4$. Y is the onium cation or alkali metal cation. The catalyst composition also comprises a phosphine ligand of the general formula

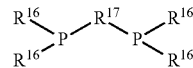

The phosphorus atoms P are bridged by 2 to 6 atoms of $R^{17}$. $R^{17}$ is selected from the group consisting of a substituted or unsubstituted alkylene, cycloalkylene, arylene, and biarylene, each having up to 22 carbon atoms. A heteroatom, optionally, can substitute for one or more of the carbon atoms. The heteroatom can be nitrogen, oxygen, sulfur, phosphorus or mixtures thereof. $R^{16}$ can be substituted or unsubstituted alkyl, alkoxy, cycloalkyl, aryl, or aryloxy, each having up to 20 carbon atoms.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

It is to be understood that the mention of one or more process steps does not preclude the presence of additional process steps before or after the combined recited steps or intervening process steps between those steps expressly identified. Moreover, the lettering of process steps or ingredients is a convenient means for identifying discrete activities or ingredients and the recited lettering can be arranged in any sequence, unless otherwise indicated.

As used herein, the singular forms "a", "an", and "the" include plural referents unless the context clearly dictates otherwise. For example, reference to a complex of cobalt iodide and an onium cation is intended to include multiple complexes of cobalt iodide and onium cations.

As used herein the term "and/or", when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The term "crude reductive carbonylation product", as used herein, refers to the reaction products of carbon monoxide and an alcohol, and optionally hydrogen. The crude reductive carbonylation product comprises the many different compounds produced under reductive carbonylation conditions. The crude reductive carbonylation product is the liquid effluent directly exiting the reductive carbonylation reactor, before any separation of the homogeneous catalyst or other liquid compounds. The crude reductive carbonylation product comprises the homologous aldehyde, homologous acid, and/or homologous alcohol, unreacted feed, and other byproducts, as well as the catalyst.

The term "catalyst", as used herein, has its typical meaning to one skilled in the art as a substance that increases the rate of chemical reactions without being consumed. The term "catalyst composition", as used herein refers to a catalyst comprising a cobalt complex and a phosphine ligand.

The term "complex", "coordination complex" and "metal complex" as used herein, are equivalent terms which have their typical meaning to one skilled in the art as a metal ion and a surrounding array of bound molecules.

The term "onium cation", as used herein, refers to a cation selected from quaternary atoms or radicals such as quaternary ammonium, quaternary phosphonium, trialkyl sulfonium, and alkylated sulfoxide. The onium cation can also be of N-alkylated pyridinium. The term "onium salt", as used herein refers to a salt containing an onium cation. One skilled in the art will recognize that the disclosure of any onium salt necessarily and simultaneously discloses the corresponding onium cation.

The term "alkali metal cation", as used herein, refers to a group one element of the periodic table excluding hydrogen having at least one more proton than electron.

The term "phosphine ligand", as used herein, refers to an organic compound composed of hydrocarbyl groups covalently bound to one or more phosphorus atoms in the +3 oxidation state such that the lone pair of at least one of the phosphorus atoms binds the cobalt when dissolved in solution with cobalt. Such ligands are commonly referred to as tertiary phosphine since the phosphorus atom is substituted by three groups.

The term "bridged by" a number of atoms, as used herein, refers to the smallest number of consecutive atoms in a path between two atoms, specifically the two phosphorus atoms. For example, 1,3-bis(diphenyl phosphino)propane is bridged by 3 carbon atoms, 1,4-bis(diphenylphosphino) butane is bridged by 4 carbon atoms, 1,2-bis(diphenylphosphino)benzene is bridged by 2 carbon atoms, bis(diphenylphosphinomethyl)biphenyl is bridged by 6 carbon atoms, and 1,1,1-tris(diphenylphosphinomethyl)ethane is bridged by 3 carbon atoms.

The term "alkylene", as used herein, refers to an alkylenediyl group having free valences at each group end to bond to the two phosphorus atoms. The terms "cycloalkylene", "arylene", and "biarylene" are used in a like manner. When the term "substituted or unsubstituted" is followed by a listing of hydrocarbon groups, the term is intended to modify each group. When a listing of hydrocarbon groups is followed by the term, "each having up to [a number of] carbon atoms", the term is intended to modify each group. The term "substituted", as used herein, has its usual meaning in the art, as in the hydrogen on the hydrocarbon may be substituted with the stated group. The term "heteroatom", as used herein has its usual meaning in the art, as an atom, such as nitrogen, oxygen, sulfur, or phosphorous, substituted for a carbon atom in a hydrocarbon.

The term "homologous aldehyde", as used herein, refers to an aldehyde containing one more carbon atom than the alcohol used to produce it. For example, n-propionaldehyde is the homologous aldehyde of ethanol reductive carbonylation. The term "homologous aldehyde equivalents", as used herein refers to the common products and byproducts containing at least one aldehyde group. The specific homologous aldehyde equivalents for methanol, ethanol, and propanol reductive carbonylation are given in the specification.

The term "homologous acid", as used herein, refers to an acid containing one more carbon atom than the alcohol used to produce it. For example, n-propionic acid is the homologous acid of ethanol reductive carbonylation. The term "homologous acid equivalents", as used herein refers to the common products and byproducts containing at least one acid group. The specific homologous acid equivalents for methanol, ethanol, and propanol reductive carbonylation are given in the specification.

The term "homologous alcohol", as used herein, refers to an alcohol containing one more carbon atom than the alcohol used to produce it. For example, n-propanol is the homologous alcohol of ethanol reductive carbonylation. The term "homologous alcohol equivalents", as used herein refers to the common products and byproducts containing at least one alcohol group. The specific homologous alcohol equivalents for methanol, ethanol, and propanol reductive carbonylation are given in the specification.

The term "higher mole percent" as used herein, refers to a larger number of moles of one component than another component in a mixture. For example, if a crude reductive carbonylation product contains 60 mole percent acetaldehyde equivalents, 30 mole percent acetic acid equivalents, and 10 mole percent ethanol equivalents, on a total acetaldehyde equivalents, acetic acid equivalents, and ethanol equivalents basis, then the crude reductive carbonylation product has a higher mole percent of acetaldehyde equivalents than either of acetic acid equivalents or ethanol equivalents. In the specific example, the crude reductive carbonylation product has 60-30=30 mole percent higher acetaldehyde equivalents than acetic acid equivalents and 60-10=50 mole percent higher acetaldehyde equivalents than ethanol equivalents.

The term "co-catalyst" as used herein, refers to a second catalyst which impacts the reaction rate and/or the selectivity to a given product.

The catalyst composition of the present invention can be used, for example, in the reductive carbonylation of a low molecular weight alcohol to its homologous aldehyde. The catalyst composition comprises a complex of cobalt, iodide, and an onium cation or an alkali metal cation of the general formula $Y_2CoI_4$, and a phosphine ligand.

The complex can be readily synthesized by those skilled in the art. For example, an onium iodide salt or alkali metal iodide salt can be reacted with cobalt(II) iodide as illustrated in the reaction below.

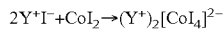

$$2Y^+I^- + CoI_2 \rightarrow (Y^+)_2[CoI_4]^{2-}$$

When an onium salt is used to produce the complex, the onium salt can comprise an onium cation selected from quaternary atoms or radicals such as quaternary ammonium, quaternary phosphonium, trialkyl sulfonium, and alkylated sulfoxide. The onium salt compound can be functional and includes protonated forms of the atoms or radicals, especially protonated forms of various tertiary amines and tertiary phosphines. The onium salt can contain any number of carbon atoms, e.g., up to about 60 carbon atoms, and also can contain one or more heteroatoms. The tri- and tetra-alkyl quaternary ammonium and phosphonium salts typically contain a total of about 5 to 40 carbon atoms. One skilled in the art understands that the listing of the onium salts simultaneously gives a listing of the onium cations (e.g., if onium salt methyltriphenylphosphonium iodide is disclosed, then onium cation methyltriphenylphosphonium is also disclosed).

Examples of an alkali metal cation include cations of lithium, sodium, potassium, rubidium and cesium. In one aspect, the alkali metal cation can be lithium, sodium, potassium, rubidium, or cesium. In another aspect, the alkali metal cation can be lithium, sodium, or potassium.

Examples of quaternary ammonium and phosphonium salts include salts having onium cations of the general formula (I)

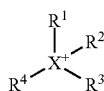

(I)

wherein X can be phosphorus (P) or nitrogen (N) and wherein $R^1$, $R^2$, $R^3$, and $R^4$ independently can be substituted or unsubstituted alkyl having up to 20 carbon atoms, substituted or unsubstituted cycloalkyl having 5 to 20 carbon atoms, or substituted or unsubstituted aryl having 6 to 20 carbon atoms.

In one aspect, X can be phosphorus (P) or nitrogen (N), $R^1$ is methyl, and $R^2$, $R^3$, and $R^4$ can be independently an alkyl having up to 12 carbons or an aryl. When $R^2$, $R^3$, and/or $R^4$ are aryl, the aryl is selected from only one of the group consisting of phenyl, tolyl, xylyl, and mesityl.

The quaternary ammonium salts can also be selected from salts of aromatic, heterocyclic onium cations having the general formula (II) or (III)

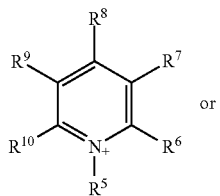

(II)

or

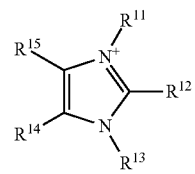

(III)

wherein at least one ring atom is a quaternary nitrogen atom and $R^6$, $R^7$, $R^8$, $R^9$, $R^{10}$, $R^{12}$, $R^{14}$, and $R^{15}$ are independently selected from hydrogen, substituted or unsubstituted alkyl having up to 20 carbon atoms, substituted or unsubstituted cycloalkyl having 5 to 20 carbon atoms, and substituted or unsubstituted aryl having 6 to 20 carbon atoms; and $R^5$, $R^{11}$, and $R^{13}$ are independently selected from substituted or unsubstituted alkyl having up to 20 carbon atoms, substituted or unsubstituted cycloalkyl having 5 to 20 carbon atoms, and substituted or unsubstituted aryl having about 6 to about 20 carbon atoms. In one aspect, $R^5$ is methyl and $R^6$, $R^7$, $R^8$, $R^9$, and $R^{10}$ are hydrogen.

Examples of specific ammonium salts include tetrapentylammonium iodide, tetrahexylammonium iodide, tetraoctyl-ammonium iodide, tetradecylammonium iodide, tetradodecylammonium iodide, tetrapropylammonium iodide, tetrabutylammonium iodide, methyltrioctylammonium iodide, methyltributylammonium iodide, N-octyl-quinuclidinium iodide, N,N'-dimethyl-N,N'-dihexadecylpiperazinium diiodide, dimethyl-hexadecyl-[3-pyrrolidinyl propyl]ammonium iodide, N,N,N,N',N',N'-hexa(dodecyl) octane-1,8-diammonium diiodide, N,N,N,N',N',N'-hexa(dodecyl)butane-1,4-diammonium diiodide; imidazolium iodides such as 1-butyl-3-methylimidazolium iodide, 1,3-dimethylimidazolium iodide, 1,3,4-trimethyl-imidazolium iodide, 1,2,3,4,5-pentamethylimidazolium iodide; pyridinium iodides such as N-octylpyridinium iodide, N-methylpyridinium iodide, N-methyl-2-picolinium iodide, N-methyl-3-picolinium iodide, N-methyl-4-picolinium iodide, N-methyl-5-ethyl-2-methyl-pyridinium iodide, N-methyl-3,4-lutidinium iodide; N-methyl quinolinium iodide, N-methyl isoquinolinium iodide or mixtures thereof. Preferred quaternary ammonium iodides include 1-butyl-3-methylimidizolium iodide, N-methyl pyridinium iodide, N-methyl-2-methyl pyridinium iodide, N-methyl-3-methyl pyridinium iodide, N-methyl-4-methyl pyridinium iodide, or 1,3-dimethylimidazolium iodide.

Exemplary phosphonium salts include tetraoctylphosphonium iodide, tetrabutylphosphonium iodide, triphenyl(hexyl)phosphonium iodide, triphenyl(octyl)phosphonium iodide, tribenzyl(octyl)phosphonium iodide, tribenzyl(dodecyl)phosphonium iodide, triphenyl(decyl)phosphonium iodide, triphenyl(dodecyl)phosphonium iodide, tetrakis(2-methylpropyl)phosphonium iodide, tris(2-methylpropyl) (butyl)phosphonium iodide, triphenyl(3,3-dimethylbutyl) phosphonium iodide, triphenyl(3-methylbutyl)phosphonium iodide, tris(2-methylbutyl)(3-methylbutyl)phosphonium iodide, triphenyl[2-trimethylsilylethyl]phosphonium iodide, tris(p-chlorophenyl)-(dodecyl)phosphonium iodide, hexyltris(2,4,6-trimethylphenyl)phosphonium iodide, tetradecyltris(2,4,6-trimethylphenyl)phosphonium iodide, dodecyltris (2,4,6-trimethylphenyl)phosphonium iodide, methyltrioctylphosphonium iodide, methyltributylphosphonium iodide, methyl-tricyclohexylphosphonium iodide, and the like. Preferred phosphonium iodides include methyltriphenylphosphonium iodide, methyltributylphosphonium iodide, or methyltrioctylphosphonium iodide.

In one aspect, the onium cation can be of the general formula (I) or (II)

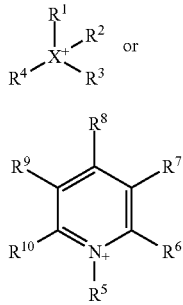

X can be phosphorus (P) or nitrogen (N), $R^1$ is methyl, and $R^2$, $R^3$, and $R^4$ independently can be an alkyl having up to 12 carbon atoms or an aryl, wherein the aryl is selected from only one of the group consisting of phenyl, tolyl, xylyl, and mesityl; $R^5$ is methyl and $R^6$, $R^7$, $R^8$, $R^9$, and $R^{10}$ are hydrogen. In another aspect, the onium cation is of formula (I), where X is phosphorus (P), $R^1$ is methyl, and $R^2$, $R^3$, and $R^4$ independently can be an alkyl having up to 12 carbons or an aryl. When $R^2$, $R^3$, and/or $R^4$ are aryl, the aryl groups are the same and can be phenyl, tolyl, xylyl, or mesityl.

In one aspect, the onium cation can be methyltriphenylphosphonium, methyltributylphosphonium, methyltrioctylphosphonium, or 1-methylpyridinium. In another aspect, the onium cation can be methyltriphenylphosphonium, methyltributylphosphonium, or 1-methylpyridinium. In another aspect, the onium cation can be methyltriphenylphosphonium or 1-methylpyridinium. In one aspect, the complex can be bis(methyltriphenylphosphonium) cobalt tetraiodide, bis(methyltributylphosphonium) cobalt tetraiodide, or bis(1-methylpyridinium) cobalt tetraiodide.

In one aspect of the invention, the onium salt can be generated from polymers containing a quaternary or quaternizable phosphine or amine. The onium salt polymer may be derived in whole or part from (or containing polymerized residues of) 2- or 4-vinyl-N-alkylpyridinium iodide or 4-(trialkyl-ammonium)styrene iodide. For example, a variety of 4-vinyl pyridine polymers and copolymers are available, and may be quaternized or protonated with alkyl iodide or hydrogen iodide to generate heterogeneous onium salts. Further, polymers of N-methyl-4-vinylpyridinium chloride are commercially available and may be used as-is or are preferably exchanged with iodide by well-known means to form the iodide salt. The heterogeneous onium compound may comprise (1) an onium salt compound deposited on a catalyst support material or (2) of a polymeric material containing quaternary nitrogen groups. Examples of such polymeric onium compounds include polymers and copolymers of vinyl monomers which contain quaternary nitrogen (ammonium) groups. Polymers and copolymers derived from 2- and 4-vinyl-N-alkylpyridinium iodide, e.g., poly(4-vinyl-N-methylpyridinium iodide), are specific examples of such polymeric onium salt compounds. In this aspect, the onium cation would be a heterogeneous component in the reaction mixture.

The catalyst composition of the invention comprises a cobalt complex and a phosphine ligand. The phosphine ligand is a multidentate compound containing at least two bridged phosphorus atoms. The phosphine ligand can be of the general formula

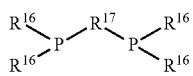

The phosphorus atoms P are bridged by 2 to 6 atoms of $R^{17}$. $R^{17}$ can be a substituted or unsubstituted alkylene, cycloalkylene, arylene and/or biarylene, each having up to 22 carbon atoms. $R^{17}$ can optionally contain one or more heteroatoms. The heteroatom can be nitrogen, oxygen, sulfur, phosphorus, or mixtures thereof. $R^{16}$ is a substituted or unsubstituted alkyl, alkoxy, cycloalkyl, aryl, and/or aryloxy, each having up to 20 carbon atoms.

The phosphorus atoms P are bridged by 2 to 6 atoms which means that the shortest molecular path between the two phosphorus atoms contains 2 to 6 atoms. These 2 to 6 atoms are referred to as bridging atoms. The bridging atoms can be carbon and/or heteroatom selected from nitrogen, oxygen, sulfur, phosphorus or mixtures thereof.

In one example, $R^{17}$ can be a straight- or branch-chain hydrocarbon radical containing 2 to 6 bridging atoms, where the bridging atoms can be substituted, for example, with alkyl, alkoxy, aryl, dialkylphosphinomethyl, diarylphosphino, or diarylphosphinomethyl.

In another aspect, $R^{17}$ can be arylene or biarylene. The arylene or biarylene can be substituted, for example, with methyl, ethyl, propyl, iso-propyl, butyl, iso-butyl, methoxy, ethoxy, propoxy, iso-propoxy, butoxy, iso-butoxy, phenoxy, nitro, chloro, fluoro, trifluoromethyl. In another aspect, the arylene or biarylene can be substituted with methyl, ethyl, propyl, or iso-propyl.

In one aspect, $R^{16}$ can be a substituted alkyl, alkoxy, cycloalkyl, aryl, or aryloxy wherein the substituted group can be, for example, methyl, ethyl, propyl, iso-propyl, butyl, iso-butyl, methoxy, ethoxy, propoxy, iso-propoxy, butoxy, iso-butoxy, phenoxy, nitro, chloro, fluoro, or trifluoromethyl. In another aspect, the substituted group can be methyl, ethyl, propyl, or iso-propyl.

In one aspect, $R^{16}$ is chosen from phenyl, naphthyl, anthryl, tetrahydronaphthyl, or octahydronaphthyl each of which can be substituted with alkyl, alkoxy, aryl, aryloxy, halogen, or nitro. In one aspect, $R^{16}$ can be methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, or mesityl-oxy Without representing an exhaustive list, specific examples of multidentate phosphine ligands useful in the present invention include 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1-tris(diphenylphosphinomethyl)ethane; 1,1,1-tris(diethylphosphinomethyl)ethane; 1,5-bis(diphenylphosphino)pentane; 1,2-bis(dicyclohexylphosphino)ethane; 1,3-bis(dicyclohexylphosphino)propane; 1,4-bis(dicyclohexylphosphino)butane; 1,5-bis(dicyclohexylphosphino)pentane; 1,6-bis(dicyclohexylphosphino)hexane; 1,2-bis(dimethylphosphino)ethane; 1,3-bis(dimethylphosphino)propane; 1,4-bis(dimethylphosphino)butane; 1,5-bis(dimethylphosphino)pentane; 1,6-bis(dimethylphosphino)hexane; 1,2-bis(diisopropylphosphino)ethane; 1,3-bis(diisopropylphosphino)propane; 1,4-bis(diisopropylphosphino)butane; 1,2-bis(di-tert-butylphosphine)ethane; 1,3-bis(di-tert-butylphosphino)

propane; 1,4-bis(di-tert-butyl phosphine)butane; 2,2'-bis(diphenylphosphino)-1,1'-binaphthalene; 2,2'-bis(diphenylphosphino)-1,1'-biphenyl; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and/or 1,3-bis(diphenylphosphino)cyclobutane.

In one aspect the phosphine ligand can be chosen from 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1-tris(diphenylphosphinomethyl)ethane; 1,1,1-tris(diethylphosphinomethyl)ethane; 1,3-bis(dicyclohexylphosphino)propane; 1,3-bis(dimethylphosphino)propane; 1,3-bis(diisopropylphosphino)propane; 1,3-bis(di-tert-butylphosphino)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and/or 1,3-bis(diphenylphosphino)cyclobutane.

In one aspect, the phosphine ligand can be chosen from 1,3-bis(diphenylphosphino)propane; 1,1,1,-tris(diphenylphosphinomethyl)ethane; 1,1,1-tris(diethylphosphinomethyl)ethane; 1,3-bis(dicyclohexylphosphino)propane; 1,3-bis(dimethylphosphino)propane; 1,3-bis(diisopropylphosphino)propane; 1,3-bis(di-tert-butylphosphino)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and/or 1,3-bis(diphenylphosphino)cyclobutane.

In one aspect the phosphine ligand can be 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1-tris(diphenylphosphinomethyl)ethane; and/or 1,1,1-tris(diethylphosphinomethyl)ethane. In one aspect, the phosphine ligand can be 1,3-bis(diphenylphosphino)propane, 1,1,1,-tris(diphenylphosphinomethyl)ethane, and/or 1,1,1-tris(diethylphosphinomethyl)ethane.

In one aspect, the phosphorus atoms are bridged by saturated or unsaturated alkylene containing three carbon atoms. The phosphine ligand can be of the general formula

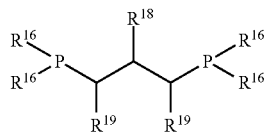

In one aspect, $R^{18}$ can be a hydrogen radical or a hydrocarbon radical having up to 17 carbon atoms. The hydrocarbon radical can be substituted with alkyl, alkoxy, cycloalkyl aryl, aryloxy dialkylphosphinomethyl, diarylphosphinomethyl, or mixtures thereof. In another aspect, $R^{18}$ can be a hydrogen radical, methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, mesityl-oxy, dimethylphosphinomethyl, diethylphosphinomethyl, di-n-propylphosphinomethyl, di-iso-propylphosphinomethyl, di-n-butylphosphinomethyl, di-iso-butylphosphinomethyl, di-tert-butylphosphinomethyl, dimethoxyphosphinomethyl, diethoxyphosphinomethyl, di-n-propoxyphosphinomethyl, di-iso-propoxyphosphinomethyl, di-n-butoxyphosphinomethyl, di-iso-butoxyphosphinomethyl, di-tert-butoxyphosphinomethyl diphenylphosphinomethyl, ditolylphosphinomethyl, or dixylylphosphinomethyl.

$R^{19}$ can be a hydrogen radical or a substituted or unsubstituted alkyl, alkoxy, cycloalkyl, aryl, and aryloxy, each having up to 8 carbon atoms. In one aspect, $R^{19}$ can be a hydrogen radical or a substituted or unsubstituted alkyl. In one aspect, $R^{19}$ can be a hydrogen radical.

In one aspect $R^{16}$ can be methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, or mesityl-oxy.

In one aspect, $R^{16}$ or $R^{18}$ can be unsubstituted aryl, alkyl, cycloalkyl, alkoxy, or aryloxy substituted, for example, with groups selected from methyl, ethyl, propyl, iso-propyl, butyl, iso-butyl, methoxy, ethoxy, propoxy, iso-propoxy, butoxy, iso-butoxy, phenoxy, nitro, chloro, fluoro, and/or trifluoromethyl.

In one aspect, $R^{16}$ or $R^{18}$ can be aryl groups chosen from phenyl, naphthyl, anthryl, tetrahydronaphthyl, and/or octahydronaphthyl with any of the groups substituted with alkyl, alkoxy, aryl, aryloxy, halogen, and/or nitro.

In one aspect, the phosphorus atoms are bridged by saturated or unsaturated alkylene containing three carbon atoms. The phosphine ligand can be of the general formula

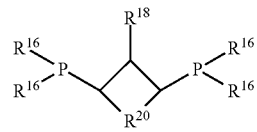

$R^{20}$ can be a substituted or unsubstituted alkyl having up to 8 carbon atoms, forming a cycloalkyl group between the phosphorus atoms. $R^{18}$ is a hydrogen radical and $R^{16}$ is selected from the group consisting of methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, and mesityl-oxy.

In one aspect, the onium cation can be methyltriphenylphosphonium, methyltributylphosphonium, methyltrioctylphosphonium, and/or 1-methylpyridinium and the phosphine ligand can be 1,3-bis(diphenylphosphino)propane, 1,1,1-tris(diphenylphosphinomethyl)ethane, and/or 1,1,1-tris(diethylphosphinomethyl)ethane. In one aspect, the onium cation can be methyltriphenylphosphonium and the phosphine ligand and be 1,3-bis(diphenylphosphino)propane.

In one aspect, the molar ratio of the phosphine ligand to the cobalt (phosphine ligand:cobalt) ranges from 0.025:1 to 2:1. In other examples, the molar ratio of phosphine ligand to cobalt (phosphine ligand:cobalt) ranges from 0.025:1 to 0.5:1 or 0.025:1 to 1:1 or 0.025:1 to 1.5:1 or 0.1:1 to 1:1 or 0.1:1 to 0.1:1.5, or 1:1 to 2:1.

The catalyst composition can further comprise a solvent. The solvent is not particularly limiting so long as it is inert under reaction conditions. Other considerations in the selection of a solvent are reactants and products for the catalyst composition use, unit price, corrosion, and the like. When using the catalyst composition for the reductive carbonylation of an alcohol comprising 1 to 3 carbon atoms, the alcohol can be the solvent.

The catalyst composition of the first embodiment can be used in a process for the reductive carbonylation of a low molecular weight alcohol to its homologous aldehyde or alcohol. A second embodiment of our invention is a process for the preparation of a crude reductive carbonylation product comprising contacting hydrogen, carbon monoxide, and an alcohol having 1 to 3 carbon atoms in the presence of a catalyst composition to form the crude reductive carbonylation product. The crude reductive carbonylation product comprises homologous aldehyde equivalents in a higher mole percent than homologous acid equivalents or homologous alcohol equivalents, each based on the total moles of the homologous aldehyde equivalents, the homologous acid equivalents, and the homologous alcohol equivalents. The catalyst composition comprises a complex of cobalt, iodide, and an onium cation or an alkali metal cation of the general formula $Y_2CoI_4$, where Y represents the onium cation or the alkali metal cation. The catalyst composition also comprises a phosphine ligand of the general formula

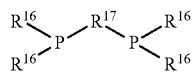

The phosphorus atoms P are bridged by 2 to 6 atoms of $R^{17}$. $R^{17}$ is selected from the group consisting of a substituted or unsubstituted alkylene, cycloalkylene, arylene, and biarylene, each having up to 20 carbon atoms. A heteroatom, optionally, can substitute for one or more of the carbon atoms. The heteroatom can be nitrogen, oxygen, sulfur, phosphorus or mixtures thereof. $R^{16}$ can be substituted or unsubstituted alkyl, alkoxy, cycloalkyl, aryl, or aryloxy, each having up to 20 carbon atoms. The crude reductive carbonylation product comprises less than 1 weight percent of methyl iodide.

It is understood that the descriptions herein above regarding, the catalyst composition, the onium cation/salts and alkali cations/salts, the phosphine ligands, and the molar ratio of phosphine ligand to cobalt apply equally well to the second embodiment.

The alcohol contacted with carbon monoxide and hydrogen in the process is an alcohol having 1 to 3 carbon atoms. In one aspect, the alcohol can be methanol, ethanol, or n-propanol. In another aspect the alcohol comprises methanol. In another aspect, the alcohol comprises ethanol. In yet another aspect, the alcohol comprises n-propanol.

In one aspect, the crude reductive carbonylation product comprises homologous aldehyde equivalents in a higher mole percent than homologous acid equivalents or homologous alcohol equivalents from the reaction of carbon monoxide, hydrogen, and the alcohol. In one aspect the alcohol comprises methanol and the crude reductive carbonylation product comprises acetaldehyde equivalents in a higher mole percent than acetic acid equivalents or ethanol equivalents, each based on the total moles of acetaldehyde equivalents, acetic acid equivalents, and ethanol equivalents. In one aspect, the alcohol comprises ethanol and the crude reductive carbonylation product comprises n-propionaldehyde equivalents in a higher mole percent than n-propionic acid equivalents or n-propanol equivalents, each based on the total moles of n-propionaldehyde equivalents, n-propionic acid equivalents, and n-propanol equivalents. In one aspect, the alcohol comprises n-propanol and the crude reductive carbonylation product comprises n-butyraldehyde equivalents in a higher mole percent than n-butyric acid equivalents, or n-butanol equivalents, each based on the total moles of n-butyraldehyde equivalents, n-butyric acid equivalents, and n-butanol equivalents.

The total moles of homologous aldehyde equivalents are determined as the sum of the moles of reductive carbonylation product compounds that have at least one aldehyde group, with the number of moles of each compound multiplied by the number of aldehyde groups in the compound. For example, when methanol is carbonylated, the homologous aldehyde equivalents are the sum of the moles Acetaldehyde+3*moles Paraldehyde+moles Acetaldehyde dimethyl acetal+moles Acetaldehyde methyl ethyl acetal+moles Acetaldehyde diethyl acetal. The total moles of homologous acid equivalents and homologous alcohol equivalents are determined in the same manner. The homologous aldehyde equivalents, homologous acid equivalents, and homologous alcohol equivalents for methanol, ethanol, and n-propanol reductive carbonylation are listed below.

For methanol reductive carbonylation, homologous aldehyde equivalents, homologous acid equivalents, and homologous alcohol equivalents—acetaldehyde equivalents, acetic acid equivalents, and ethanol equivalents—are given below.

| Acetaldehyde Equivalents | Acetic Acid Equivalents | Ethanol Equivalents |
|---|---|---|
| Acetaldehyde | Acetic acid | Ethanol |
| Acetaldehyde dimethyl acetal | Methyl acetate | Acetaldehyde diethyl acetal |
| Acetaldehyde methyl ethyl acetal | Ethyl acetate | Acetaldehyde methyl ethyl acetal |
| Acetaldehyde diethyl acetal | | Diethyl ether |
| Paraldehyde | | Methyl ethyl ether |
| | | Ethyl acetate |

For ethanol reductive carbonylation, homologous aldehyde equivalents, homologous acid equivalents, and homologous alcohol equivalents—n-propionaldehyde equivalents, n-propionic acid equivalents, and n-propanol equivalents—are given below.

| Propionaldehyde Equivalents | Propionic Acid Equivalents | Propanol Equivalents |
|---|---|---|
| Propionaldehyde | Propionic acid | 1-Propanol |
| Propionaldehyde diethyl acetal | Ethyl propionate | Propionaldehyde di-n-propyl acetal |
| Propionaldehyde n-propyl ethyl acetal | Propyl propionate | Propionaldehyde n-propyl ethyl acetal |
| Propionaldehyde di-n-propyl acetal | | Di-n-propyl ether |
| 2,4,6-triethyl-1,3,5-trioxane | | n-Propyl ethyl ether |
| | | n-Propyl propionate |

For n-propanol reductive carbonylation, homologous aldehyde equivalents, homologous acid equivalents, and homologous alcohol equivalents—n-butyraldehyde equivalents, n-butyric acid equivalents, and n-butanol equivalents—are given below.

| Butyraldehyde Equivalents | Butyric Acid Equivalents | Butanol Equivalents |
|---|---|---|
| n-Butyraldehyde | n-Butyric acid | 1-Butanol |
| n-Butyraldehyde di-n-propyl acetal | n-Propyl butyrate | n-Butyraldehyde di-n-butyl acetal |
| n-Butyraldehyde n-butyl n-propyl acetal | n-Butyl butyrate | n-Butyraldehyde n-butyl n-propyl acetal |
| n-Butyraldehyde di-n-butyl acetal | | Di-n-butyl ether |
| 2,4,6-tripropyl-1,3,5-trioxane | | n-Butyl n-propyl ether |
| | | n-Butyl butyrate |

The hydrogen and carbon monoxide contacted with an alcohol can be obtained from typical sources that are well known in the art. For example, the carbon monoxide and hydrogen can be provided by any of a number of methods known in the art including steam or carbon dioxide reforming of carbonaceous materials such as natural gas or petroleum derivatives; partial oxidation or gasification of carbonaceous materials, residuum, bituminous, sub bituminous, and anthracitic coals and cokes; lignite; oil shale; oil sands; peat; biomass; petroleum refining residues of cokes; and the like. For example, the carbon monoxide can be provided to the reaction mixture as a component of synthesis gas or "syngas", comprising carbon dioxide, carbon monoxide, and hydrogen. The hydrogen and carbon monoxide can be mixed together before the contacting, or a stream of hydrogen and a separate stream of carbon monoxide can be contacted with the alcohol.

The molar ratio of carbon monoxide to hydrogen ($CO:H_2$) can vary over a wide range. For example, $CO:H_2$, can range from 50:1 to 1:50. In other examples, $CO:H_2$ ranges from 10:1 to 1:10 or 5:1 to 1:5 or 3:1 to 1:3 or 2:1 to 1:2 or 10:1 to 1:1 or 5:1 to 1:1 or 2:1 to 1:1 or 2:1 to 1:5 or 1:1 to 1:5 or 1:1 to 1:10.

The amount of catalyst composition can be measured in terms of the moles of cobalt, the moles of phosphine ligand and/or the molar ratio of phosphine ligand to cobalt (phosphine ligand:cobalt). In one aspect, the cobalt is present in an amount ranging from 0.001 moles to 50 moles of cobalt per 100 moles of alcohol. Other examples of cobalt concentration include 0.001 moles to 10 moles of cobalt per 100 moles of alcohol, 0.01 moles to 5 moles of cobalt per 100 moles of alcohol, 0.01 moles to 2 moles of cobalt per 100 moles of alcohol, and 0.02 moles to 5 moles of cobalt per 100 moles of alcohol. In one aspect, the molar ratio of the phosphine ligand to the cobalt (phosphine ligand:cobalt) ranges from 0.025:1 to 2:1. In other examples, the molar ratio of phosphine ligand to cobalt (phosphine ligand:cobalt) ranges from 0.025:1 to 0.5:1 or 0.025:1 to 1:1 or 0.025:1 to 1.5:1 or 0.1:1 to 1:1 or 0.1:1 to 0.1:1.5, or 1:1 to 2:1. For a batch reaction, the catalyst concentration can be determined based on the moles of catalyst charged per 100 moles of alcohol charged to the batch reactor. For a continuous reaction, the catalyst concentration can be determined based on the moles of catalyst fed per 100 moles of alcohol fed to the reactor over a given time period. The catalyst and the alcohol can be fed to the reactor together or separately.

The present invention can be conducted under continuous, semi-continuous, and batch modes of operation and can utilize a variety of reactor types. The term "continuous" as used herein means a process wherein reactants are introduced and products withdrawn simultaneously in an uninterrupted manner. By "continuous" it is meant that the process is substantially or completely continuous in operation and is to be contrasted with a "batch" process. "Continuous" is not meant in any way to prohibit normal interruptions in the continuity of the process due to, for example, start-up, reactor maintenance, or scheduled shut down periods. The term "batch" process as used herein means a process wherein all the reactants are added to the reactor and then processed according to a predetermined course of reaction during which no material is fed or removed into the reactor. The term "semicontinuous" means a process where some of the reactants are charged at the beginning of the process and the remaining reactants are fed continuously as the reaction progresses. Alternatively, a semicontinuous process may also include a process similar to a batch process in which all the reactants are added at the beginning of the process except that one or more of the products are removed continuously as the reaction progresses.

Any of the known carbonylation reactor designs or configurations may be used in carrying out the process provided by the present invention. Examples of suitable reactor types include, but are not limited to, stirred tank, continuous stirred tank, tower, and tubular reactors. The process also may be practiced in a batchwise manner by contacting the low molecular weight alcohol, hydrogen and carbon monoxide with the present catalyst composition in an autoclave.

The amount of methyl iodide in the crude reductive carbonylation product is significantly less than in typical methanol reductive carbonylation processes. In one aspect, the crude reductive carbonylation product comprises less than 1 weight percent methyl iodide, based on the total weight of the crude reductive carbonylation product. In other aspects, the crude reductive carbonylation product comprises less than 0.8 weight percent, less than 0.5 weight percent, less than 0.1 weight percent, less than 0.05 weight percent, less than 100 ppm, less than 50 ppm, less than 10 ppm, less than 100 ppb, less than 50 ppb, or less than 10 ppb of methyl iodide, based on the total weight of the crude reductive carbonylation product.

The process can be carried out over a range of temperatures. For example, the process can be carried out at a temperature ranging from 100° C. to 250° C. In other examples, the process can be carried out at a temperature ranging from 150° C. to 230° C., or ranging from 170° C. to 210° C.

The process can be carried out over a range of pressures. For example, the process can be carried out at a pressure ranging from 100 kPa (15 psig) to 60 MPa bar (8700 psig). In other examples, the process can be carried out at a pressure ranging from 1 MPa (150 psig) to 40 MPa (5800 psig) or ranging from 6.9 MPa (1000 psig) to 34 MPA (4900 psig).

In one aspect of our invention, the contacting of the hydrogen, carbon monoxide, and alcohol can occur in the presence of a solvent selected from alkanes and arenes having 6 to 20 carbon atoms, ketones having 5 to 20 carbon atoms, esters having 5 to 20 carbon atoms, ethers having 5 to 20 carbon atoms, and alkyl carbonate esters having from 3 to 20 carbon atoms. Some representative examples of the solvent include, but are not limited to, hexane, heptane, octane, decane, benzene, toluene, xylenes, methyl napththalenes, 3-methyl-2-butanone, methyl isobutyl ketone (also known as 4-methyl-2-pentanone), methyl isopropyl ketone, methyl propyl ketone, diisobutyl ketone, isobutylisobutyrate, ethyl acetate, n-butyl acetate, isobutylacetate, isopropylacetate, n-propyl acetate, diisopropylether, dibutylether, tertiary-amyl methyl ether, tertiary-butyl methyl ether, and mixtures thereof. In one aspect of our invention, the solvent can be toluene, heptane, cyclohexane, ethylbenzene, diethyl ether, or 4-methylanisol.

The amount of solvent used is not critical to the subject invention. For example, the solvent can be present in an amount ranging from 5 vol % to 90 vol % based on the total volume of solvent and alcohol. In other examples, the solvent can be present in an amount ranging from 10 vol % to 80 vol %: 20 vol % to 60 vol %: or 30 vol % to 50 vol %, each based on the total volume of solvent and alcohol.

A third embodiment of our invention is a process for the preparation of a crude reductive carbonylation product comprising contacting hydrogen, carbon monoxide, and methanol in the presence of a catalyst composition to form the crude reductive carbonylation product. The crude reductive carbonylation product comprises acetaldehyde equivalents in a higher mole percent than acetic acid equivalents or ethanol equivalents, each based on the total moles of the acetaldehyde equivalents, the acetic acid equivalents, and the ethanol equivalents. The catalyst composition comprises a complex of cobalt, iodide, and an onium cation of the general formula $Y_2CoI_4$, where Y represents the onium cation. The onium cation is of the general formula (I) or (II)

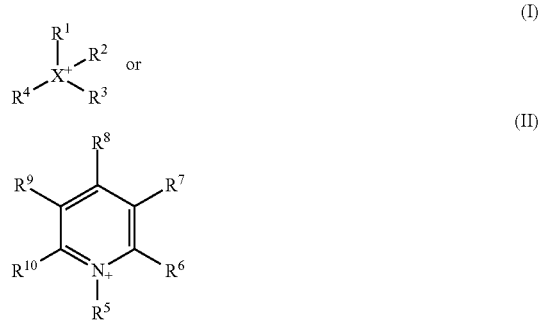

For formula (I), X is phosphorus (P) and $R^1$ is methyl. $R^2$, $R^3$, and $R^4$ are independently selected from alkyl having up to 12 carbons and aryl. When $R^2$, $R^3$, and/or $R^4$ are aryl, each aryl is the same, and can be phenyl, tolyl, xylyl, or mesityl. For formula (II), $R^5$ is methyl and $R^6$, $R^7$, $R^8$, $R^9$, and $R^{10}$ are hydrogen. The catalyst composition also comprises a phosphine ligand. The phosphine ligand can be 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1-tris(diphenylphosphinomethyl)ethane; 1,1,1-tris(diethylphosphinomethyl)ethane; 1,3-bis(dicyclohexylphosphino)propane; 1,3-bis(dimethylphosphino)propane; 1,3-bis(diisopropylphosphino)propane; 1,3-bis(di-tert-butylphosphino)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and/or 1,3-bis(diphenylphosphino)cyclobutane. The crude reductive carbonylation product comprises less than 1 weight percent of methyl iodide.

It is understood that the descriptions herein above regarding the catalyst composition, the onium cations/salts, the phosphine ligands, the molar ratio of phosphine ligand to cobalt, methanol reductive carbonylation reactions and the corresponding products, carbon monoxide and hydrogen feed, $CO:H_2$, the level of methyl iodide in the crude reductive carbonylation product, pressure, temperature, and solvent apply equally well to the third embodiment.

In one aspect, the phosphine ligand can be 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1-tris(diphenylphosphinomethyl)ethane; 1,1,1-tris(diethylphosphinomethyl)ethane. In another aspect, onium cation can be methyltriphenylphosphonium, methyltributylphosphonium, methyltrioctylphosphonium, or 1-methylpyridinium and the phosphine ligand can be 1,3-bis(diphenylphosphino)propane; 1,1,1-tris(diphenylphosphinomethyl)ethane; and/or 1,1,1-tris(diethylphosphinomethyl)ethane.

In further aspects, the molar ratio of carbon monoxide to hydrogen ($CO:H_2$) can range from 10:1 to 1:10, 5:1 to 1:5, or 3:1 to 1:3. The cobalt can be present in an amount ranging from 0.02 moles to 5 moles of cobalt per 100 moles of methanol and the molar ratio of the phosphine ligand to cobalt (phosphine ligand:cobalt) can range from 0.025:1 to 2:1. The process can be carried out at a temperature ranging from 150° C. to 230° C. and a pressure ranging from 1 MPa (150 psig) to 40 MPa (5800 psig) or ranging from 6.9 MPa (1000 psig) to 34 MPA (4900 psig). The contacting can further occur in the presence of a solvent where the solvent can be toluene, heptane, cyclohexane, ethylbenzene, diethyl ether, or 4-methylanisole.

A fourth embodiment of our invention is a process for the preparation of a crude reductive carbonylation product comprising contacting hydrogen, carbon monoxide, and an alcohol having 1 to 3 carbon atoms in the presence of a catalyst composition to form the crude reductive carbonylation product. The crude reductive carbonylation product comprises homologous alcohol equivalents in a higher mole percent than homologous aldehyde equivalents or homologous acid equivalents, each based on the total moles of the homologous aldehyde equivalents, the homologous acid equivalents, and the homologous alcohol equivalents. The catalyst composition comprises a complex of cobalt, iodide, and an onium cation or an alkali metal cation of the general formula $Y_2CoI_4$, where Y represents the onium cation or the alkali metal cation. The catalyst composition also comprises a phosphine ligand of the general formula

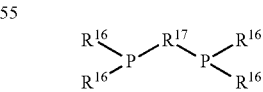

The phosphorus atoms P are bridged by 2 to 6 atoms of $R^{17}$. $R^{17}$ is selected from the group consisting of a substituted or unsubstituted alkylene, cycloalkylene, arylene, and biarylene, each having up to 22 carbon atoms. A heteroatom, optionally, can substitute for one or more of the carbon atoms. The heteroatom can be nitrogen, oxygen, sulfur, phosphorus or mixtures thereof. $R^{16}$ can be substituted or unsubstituted alkyl, alkoxy, cycloalkyl, aryl, or aryloxy, each having up to 20 carbon atoms. The process further comprises a ruthenium co-catalyst. The crude reductive carbonylation product comprises less than 1 weight percent of methyl iodide.

It is understood that the descriptions herein above regarding, the catalyst composition, the onium cations/salts and alkali cations/salts, the phosphine ligands, the molar ratio of phosphine ligand to cobalt, carbon monoxide and hydrogen feed, the level of methyl iodide in the crude reductive carbonylation product, pressure, temperature, and solvent apply equally well to the fourth embodiment.

The alcohol contacted with carbon monoxide and hydrogen in the process is an alcohol having 1 to 3 carbon atoms. In one aspect, the alcohol is selected from the group consisting of methanol, ethanol, and n-propanol. In another aspect the alcohol comprises methanol. In another aspect the alcohol comprises ethanol. In yet another aspect the alcohol comprises n-propanol.

In one aspect, the crude reductive carbonylation product comprises homologous alcohol equivalents in a higher mole percent than homologous aldehyde equivalents or homologous acid equivalents from the reaction of carbon monoxide, hydrogen, and the alcohol. In one aspect the alcohol comprises methanol and the crude reductive carbonylation product comprises ethanol equivalents in a higher mole percent than acetaldehyde equivalents or acetic acid equivalents, each based on the total moles of acetaldehyde equivalents, acetic acid equivalents, and ethanol equivalents. In one aspect, the alcohol comprises ethanol and the crude reductive carbonylation product comprises n-propanol equivalents in a higher mole percent than n-propionaldehyde equivalents or n-propionic acid equivalents, each based on the total moles of n-propionaldehyde equivalents, n-propionic acid equivalents, and n-propanol equivalents. In one aspect, the alcohol comprises n-propanol and the crude reductive carbonylation product comprises n-butanol equivalents in a higher mole percent than n-butyraldehyde equivalents, or n-butyric acid equivalents, each based on the total moles of n-butyraldehyde equivalents, n-butyric acid equivalents, and n-butanol equivalents.

The molar ratio of carbon monoxide to hydrogen ($CO:H_2$) can vary over a wide range. For example, $CO:H_2$, can range from 1:1 to 1:10. In other examples, $CO:H_2$ ranges from 1:1 to 1:5 or 1:1 to 1:2.

In order to increase selectivity of the reductive carbonylation reaction from homologous aldehyde equivalents to homologous alcohol equivalents, the addition of a co-catalyst can be useful. This co-catalyst can be chosen from any metal capable of hydrogenating an aldehyde such as iridium, rhodium, or ruthenium. Ruthenium is the most often used. The source of ruthenium is not particularly limiting and can be chosen from many commercially available materials such as ruthenium(III) acetylacetonate, ruthenium trichloride, triruthenium dodecacarbonyl, 1,1,1-tris(diphenylphosphinomethyl)ethane ruthenium, and ruthenium(IV)oxide hydrate. In one aspect the co-catalyst can be selected from triruthenium dodecacarbonyl, 1,1,1-tris(diphenylphosphinomethyl)ethane ruthenium dicarbonyl, and ruthenium(IV) oxide hydrate. In one aspect, the co-catalyst is present in an amount ranging from 0.0001 moles to 10 moles of co-catalyst per 100 moles of alcohol. Other examples of co-catalyst concentration include 0.001 moles to 5 moles of co-catalyst per 100 moles of alcohol and 0.001 moles to 2 moles of co-catalyst per 100 moles of alcohol.

Listing of Non-Limiting Embodiments

Embodiment A is a catalyst composition comprising a complex of cobalt, iodide, and an onium cation or an alkali metal cation of the general formula $Y_2CoI_4$. Y is the onium cation or alkali metal cation. The catalyst composition also comprises a phosphine ligand of the general formula

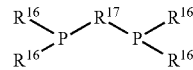

The phosphorus atoms P are bridged by 2 to 6 atoms of $R^{17}$. $R^{17}$ is selected from the group consisting of a substituted or unsubstituted alkylene, cycloalkylene, arylene, and biarylene, each having up to 22 carbon atoms. A heteroatom, optionally, can substitute for one or more of the carbon atoms. The heteroatom can be nitrogen, oxygen, sulfur, phosphorus or mixtures thereof. $R^{16}$ can be substituted or unsubstituted alkyl, alkoxy, cycloalkyl, aryl, or aryloxy, each having up to 20 carbon atoms.

The catalyst composition of Embodiment A wherein the onium cation is of the general formula (I) or (II)

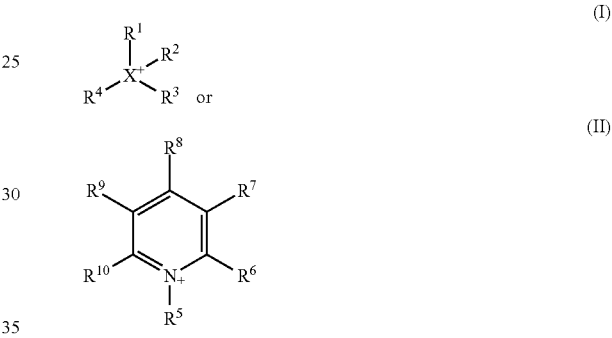

X can be phosphorus (P) or (N), $R^1$ is methyl and $R^2$, $R^3$, and $R^4$ are independently selected from alkyl having up to 12 carbons and aryl, wherein when $R^2$, $R^3$, and/or $R^4$ are aryl, each aryl is the same, and can be phenyl, tolyl, xylyl, or mesityl: or the onium cation is formula (II), $R^5$ is methyl and $R^6$, $R^7$, $R^8$, $R^9$, and $R^{10}$ are hydrogen: or the onium cation is selected from the group consisting of methyltriphenylphosphonium, methyltributylphosphonium, methyltrioctylphosphonium, and 1-methylpyridinium: or the onium cation is selected from the group consisting of methyltriphenylphosphonium and 1-methylpyridinium: or the onium cation comprises methyltriphenylphosphonium: or the alkali metal cation is selected from the group consisting of lithium, sodium, potassium, rubidium, and cesium: or the alkali metal cation is selected from the group consisting of lithium, sodium, potassium: or the complex is selected from the group consisting of bis(methyltriphenylphosphonium) cobalt tetraiodide, bis(methyltributylphosphonium) cobalt tetraiodide, bis(methyltrioctylphosphonium), and bis(1-methylpyridinium) cobalt tetraiodide.

The catalyst composition of Embodiment A or Embodiment A with one or more of the intervening features wherein the phosphine ligand is selected from the group consisting of 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1-tris(diphenylphosphinomethyl)ethane; 1,1,1-tris(diethylphosphinomethyl)ethane; 1,3-bis(dicyclohexylphosphino)propane; 1,3-bis(dimethylphosphino)propane; 1,3-bis (diisopropylphosphino)propane; 1,3-bis(di-tert-butylphosphino)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and 1,3-bis(diphenylphosphino)cyclobutane: or the phosphine ligand is selected from the group consisting of 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1-tris(diphenylphosphinomethyl)ethane; and 1,1,1-tris(diethylphosphinomethyl)ethane: or the phosphine ligand is selected from the group consisting of 1,3-bis(diphenylphosphino)propane; 1,1,1,-tris(diphenylphosphinomethyl)ethane; and 1,1,1-tris(diethylphosphinomethyl)ethane: or the phosphine ligand comprises 1,3-bis(diphenylphosphino)propane.

The catalyst composition of Embodiment A or Embodiment A with one or more of the intervening features wherein the molar ratio of phosphine ligand to cobalt (phosphine ligand:cobalt) ranges from 0.025:1 to 2:1 or ranges from 0.025:1 to 1:1.

Embodiment B is a process for the preparation of a crude reductive carbonylation product comprising contacting hydrogen, carbon monoxide, and an alcohol having 1 to 3 carbon atoms in the presence of a catalyst composition to form the crude reductive carbonylation product. The crude reductive carbonylation product comprises homologous aldehyde equivalents in a higher mole percent than homologous acid equivalents or homologous alcohol equivalents, each based on the total moles of the homologous aldehyde equivalents, the homologous acid equivalents, and the homologous alcohol equivalents. The catalyst composition comprises a complex of cobalt, iodide, and an onium cation or an alkali metal cation of the general formula $Y_2CoI_4$, where Y represents the onium cation or the alkali metal cation. The catalyst composition also comprises a phosphine ligand of the general formula

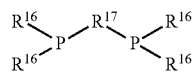

The phosphorus atoms P are bridged by 2 to 6 atoms of $R^{17}$. $R^{17}$ is selected from the group consisting of a substituted or unsubstituted alkylene, cycloalkylene, arylene, and biarylene, each having up to 22 carbon atoms. A heteroatom, optionally, can substitute for one or more of the carbon atoms. The heteroatom can be nitrogen, oxygen, sulfur, phosphorus or mixtures thereof. $R^{16}$ can be substituted or unsubstituted alkyl, alkoxy, cycloalkyl, aryl, or aryloxy, each having up to 20 carbon atoms. The crude reductive carbonylation product comprises less than 1 weight percent of methyl iodide.

The process of Embodiment B wherein the onium cation is of the general formula (I) or (II)

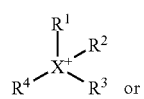

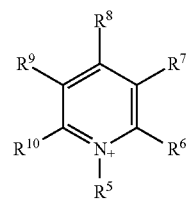

X can be phosphorus (P) or (N), $R^1$ is methyl and $R^2$, $R^3$, and $R^4$ are independently selected from alkyl having up to 12 carbons and aryl, wherein when $R^2$, $R^3$, and/or $R^4$ are aryl, each aryl is the same, and can be phenyl, tolyl, xylyl, or mesityl: or the onium cation is formula (II), $R^5$ is methyl and $R^6$, $R^7$, $R^8$, $R^9$, and $R^{10}$ are hydrogen: or the onium cation is selected from the group consisting of methyltriphenylphosphonium, methyltributylphosphonium, methyltrioctylphosphonium, and 1-methylpyridinium: or the onium cation is selected from the group consisting of methyltriphenylphosphonium and 1-methylpyridinium: or the onium cation comprises methyltriphenylphosphonium: or the alkali metal cation is selected from the group consisting of lithium, sodium, potassium, rubidium, and cesium: or the alkali metal cation is selected from the group consisting of lithium, sodium, potassium: or the complex is selected from the group consisting of bis(methyltriphenylphosphonium) cobalt tetraiodide, bis(methyltributylphosphonium) cobalt tetraiodide, bis(methyltrioctylphosphonium), and bis(1-methylpyridinium) cobalt tetraiodide.

The process of Embodiment B or Embodiment B with one or more of the intervening features wherein the phosphine ligand is selected from the group consisting of 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1-tris(diphenylphosphinomethyl)ethane; 1,1,1-tris(diethylphosphinomethyl)ethane; 1,3-bis(dicyclohexylphosphino)propane; 1,3-bis(dimethylphosphino)propane; 1,3-bis(diisopropylphosphino)propane; 1,3-bis(di-tert-butylphosphino)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and 1,3-bis(diphenylphosphino)cyclobutane: or the phosphine ligand is selected from the group consisting of 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1,-tris(diphenylphosphinomethyl)ethane; and 1,1,1-tris(diethylphosphinomethyl)ethane: or the phosphine ligand is selected from the group consisting of 1,3-bis(diphenylphosphino)propane; 1,1,1,-tris(diphenylphosphinomethyl)ethane; and 1,1,1-tris(diethylphosphinomethyl)ethane: or the phosphine ligand comprises 1,3-bis(diphenylphosphino)propane.

The process of Embodiment B or Embodiment B with one or more of the intervening features wherein the phosphine ligand to said cobalt (phosphine ligand:cobalt) ranges from 0.025:1 to 2:1 or ranges from 0.025:1 to 1:1.

The process of Embodiment B or Embodiment B with one or more of the intervening features wherein the crude reductive carbonylation product comprises homologous aldehyde equivalents in at least 10 higher mole percent, 25 higher mole percent, 50 higher mole percent, or 75 higher mole percent than homologous acid equivalents; and homologous aldehyde equivalents in at least 10 higher mole percent, 25 higher mole percent, 50 higher mole percent, or 75 higher mole percent than homologous alcohol equivalents.

The process of Embodiment B or Embodiment B with one or more of the intervening features wherein the crude reductive carbonylation product comprises less than 1 weight percent methyl iodide: or less than 500 ppm methyl iodide: or less than 10 ppm methyl iodide.

The process of Embodiment B or Embodiment B with one or more of the intervening features wherein the cobalt is present in an amount ranging from 0.001 moles to 10 moles of the cobalt per 100 moles of the alcohol; or from 0.01 moles to 5 moles of cobalt per 100 moles of alcohol, or from 0.02 moles to 5 moles of cobalt per 100 moles of alcohol.

The process of Embodiment B or Embodiment B with one or more of the intervening features wherein the process is carried out at a temperature ranging from 100° C. to 250° C.; or from 150° C. to 230° C.

The process of Embodiment B or Embodiment B with one or more of the intervening features wherein the process is carried out at a pressure ranging from 100 kPa (15 psig) to 60 MPa (8700 psig); or from 1 MPa (150 psig) to 40 MPa (5800 psig); or from 6.9 MPa (1000 psig) to 34 MPA (4900 psig).

The process of Embodiment B or Embodiment B with one or more of the intervening features wherein the molar ratio of carbon monoxide to hydrogen, $CO:H_2$, ranges from 10:1 to 1:10 or from 5:1 to 1:5.

The process of Embodiment B or Embodiment B with one or more of the intervening features wherein the contacting further occurs in the presence of a solvent selected from the group consisting of alkanes and arenes having 6 to 20 carbon atoms, ketones having 5 to 20 carbon atoms, esters having 5 to 20 carbon atoms, ethers having 5 to 20 carbon atoms, and alkyl carbonate esters having 3 to 20 carbon atoms: or wherein the contacting further occurs in the presence of a solvent selected from the group consisting of toluene, heptane, cyclohexane, ethylbenzene, diethyl ether, and 4-methylanisole.

The process of Embodiment B or Embodiment B with one or more of the intervening features and any one of the following features (1) through (3)

(1) wherein the alcohol comprises methanol and the crude reductive carbonylation product comprises acetaldehyde equivalents in a higher mole percent than acetic acid equivalents or ethanol equivalents, each based on the total moles of acetaldehyde equivalents, acetic acid equivalents, and ethanol equivalents;

(2) wherein the alcohol comprises ethanol, and the crude reductive carbonylation product comprises n-propionaldehyde equivalents in a higher mole percent than n-propionic acid equivalents or n-propanol equivalents, each based on the total moles of n-propionaldehyde equivalents, n-propionic acid equivalents, and n-propanol equivalents; or (3) wherein the alcohol comprises n-propanol and the crude reductive carbonylation product comprises n-butyraldehyde equivalents in a higher mole percent than n-butyric acid equivalents or n-butanol equivalents, each based on the total moles of n-butyraldehyde equivalents, n-butyric acid equivalents, and n-butanol equivalents.

Embodiment C is a process for the preparation of a crude reductive carbonylation product comprising contacting hydrogen, carbon monoxide, and an alcohol having 1 to 3 carbon atoms in the presence of a catalyst composition to form the crude reductive carbonylation product. The crude reductive carbonylation product comprises homologous alcohol equivalents in a higher mole percent than homologous aldehyde equivalents or homologous acid equivalents, each based on the total moles of the homologous aldehyde equivalents, the homologous acid equivalents, and the homologous alcohol equivalents. The catalyst composition comprises a complex of cobalt, iodide, and an onium cation or an alkali metal cation of the general formula $Y_2CoI_4$, where Y represents the onium cation or the alkali metal cation. The catalyst composition also comprises a phosphine ligand of the general formula

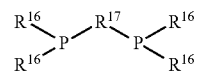

The phosphorus atoms P are bridged by 2 to 6 atoms of $R^{17}$. $R^{17}$ is selected from the group consisting of a substituted or unsubstituted alkylene, cycloalkylene, arylene, and biarylene, each having up to 22 carbon atoms. A heteroatom, optionally, can substitute for one or more of the carbon atoms. The heteroatom can be nitrogen, oxygen, sulfur, phosphorus or mixtures thereof. $R^{16}$ can be substituted or unsubstituted alkyl, alkoxy, cycloalkyl, aryl, or aryloxy, each having up to 20 carbon atoms. The process further comprises a ruthenium co-catalyst. The crude reductive carbonylation product comprises less than 1 weight percent of methyl iodide.

The process of Embodiment C wherein the onium cation is of the general formula (I) or (II)

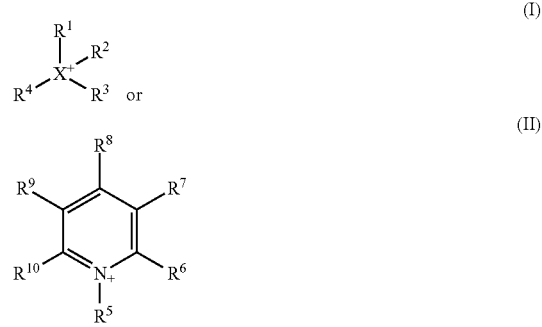

X can be phosphorus (P) or (N), $R^1$ is methyl and $R^2$, $R^3$, and $R^4$ are independently selected from alkyl having up to 12 carbons and aryl, wherein when $R^2$, $R^3$, and/or $R^4$ are aryl, each aryl is the same, and can be phenyl, tolyl, xylyl, or mesityl: or the onium cation is formula (II), $R^5$ is methyl and $R^6$, $R^7$, $R^8$, $R^9$, and $R^{10}$ are hydrogen: or the onium cation is selected from the group consisting of methyltriphenylphosphonium, methyltributylphosphonium, methyltrioctylphosphonium, and 1-methylpyridinium: or the onium cation is selected from the group consisting of methyltriphenylphosphonium and 1-methylpyridinium: or the onium cation comprises methyltriphenylphosphonium: or the alkali metal cation is selected from the group consisting of lithium, sodium, potassium, rubidium, and cesium: or the alkali metal cation is selected from the group consisting of lithium, sodium, potassium: or the complex is selected from the group consisting of bis(methyltriphenylphosphonium) cobalt tetraiodide, bis(methyltributylphosphonium) cobalt tetraiodide, bis(methyltrioctylphosphonium), and bis(1-methylpyridinium) cobalt tetraiodide.

The process of Embodiment C or Embodiment C with one or more of the intervening features wherein the phosphine ligand is selected from the group consisting of 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1-tris(diphenylphosphinomethyl)ethane; 1,1,1-tris(diethylphosphinomethyl)ethane; 1,3-bis(dicyclohexylphosphino)propane; 1,3-bis(dimethylphosphino)propane; 1,3-bis(diisopropylphosphino)propane; 1,3-bis(di-tert-butylphosphino)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and 1,3-bis(diphenylphosphino)cyclobutane: or the phosphine ligand is selected from the group consisting of 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1-tris(diphenylphosphinomethyl)ethane; and 1,1,1-tris(diethylphosphinomethyl)ethane: or the phosphine ligand is selected from the group consisting of 1,3-bis(diphenylphosphino)propane; 1,1,1,-tris(diphenylphosphinomethyl)ethane; and 1,1,1-tris(diethylphosphinomethyl)ethane.

The process of Embodiment C or Embodiment C with one or more of the intervening features wherein the cobalt is present in an amount ranging from 0.001 moles to 10 moles of the cobalt per 100 moles of the alcohol; or from 0.01 moles to 5 moles of cobalt per 100 moles of alcohol, or from 0.02 moles to 5 moles of cobalt per 100 moles of alcohol and the molar ratio of phosphine ligand to cobalt (phosphine ligand:cobalt) ranges from 0.025:1 to 2:1 or ranges from 0.025:1 to 1:1.

The process of Embodiment C or Embodiment C with one or more of the intervening features wherein the crude reductive carbonylation product comprises homologous alcohol equivalents in at least 10 higher mole percent, 25 higher mole percent, 50 higher mole percent, or 75 higher mole percent than homologous aldehyde equivalents; and homologous alcohol equivalents in at least 10 higher mole percent, 25 higher mole percent, 50 higher mole percent, or 75 higher mole percent than homologous acid equivalents.

The process of Embodiment C or Embodiment C with one or more of the intervening features wherein the crude reductive carbonylation product comprises less than 1 weight percent methyl iodide: or less than 500 ppm methyl iodide: or less than 10 ppm methyl iodide.

The process of Embodiment C or Embodiment C with one or more of the intervening features wherein the co-catalyst is present in an amount ranging from 0.0001 moles to 10 moles of the co-catalyst per 100 moles of the alcohol; or from 0.001 moles to 5 moles of co-catalyst per 100 moles of alcohol, or from 0.001 moles to 2 moles of co-catalyst per 100 moles of alcohol.

The process of Embodiment C or Embodiment C with one or more of the intervening features wherein the process is carried out at a temperature ranging from 100° C. to 250° C.; or from 150° C. to 230° C.

The process of Embodiment C or Embodiment C with one or more of the intervening features wherein the process is carried out at a pressure ranging from 100 kPa (15 psig) to 60 MPa (8700 psig); or from 1 MPa (150 psig) to 40 MPa (5800 psig); or from 6.9 MPa (1000 psig) to 34 MPA (4900 psig).

The process of Embodiment C or Embodiment C with one or more of the intervening features wherein the molar ratio of carbon monoxide to hydrogen, $CO:H_2$, ranges from 1:1 to 1:10 or from 1:1 to 1:5 or from 1:1 to 1:2.

The process of Embodiment C or Embodiment C with one or more of the intervening features wherein the contacting further occurs in the presence of a solvent selected from the group consisting of alkanes and arenes having 6 to 20 carbon atoms, ketones having 5 to 20 carbon atoms, esters having 5 to 20 carbon atoms, ethers having 5 to 20 carbon atoms, and alkyl carbonate esters having 3 to 20 carbon atoms: or wherein the contacting further occurs in the presence of a solvent selected from the group consisting of toluene, heptane, cyclohexane, ethylbenzene, diethyl ether, and 4-methylanisole.

The process of Embodiment C or Embodiment C with one or more of the intervening features wherein the co-catalysts is selected from the group consisting of ruthenium(III) acetylacetonate, ruthenium trichloride, and triruthenium dodecacarbonyl: or the co-catalysts is selected from triruthenium dodecacarbonyl, 1,1,1-tris(diphenylphosphinomethyl)ethane ruthenium dicarbonyl, and ruthenium(IV)oxide hydrate.

The process of Embodiment C or Embodiment C with one or more of the intervening features and any one of the following features (1) through (3)

(1) wherein the alcohol comprises methanol and the crude reductive carbonylation product comprises ethanol equivalents in a higher mole percent than acetaldehyde equivalents or acetic acid equivalents, each based on the total moles of acetaldehyde equivalents, acetic acid equivalents, and ethanol equivalents;

(2) wherein the alcohol comprises ethanol, and the crude reductive carbonylation product comprises n-propanol equivalents in a higher mole percent than n-propionaldehyde equivalents or n-propionic acid equivalents, each based on the total moles of n-propionaldehyde equivalents, n-propionic acid equivalents, and n-propanol equivalents; or (3) wherein the alcohol comprises n-propanol and the crude reductive carbonylation product comprises n-butanol equivalents in a higher mole percent than n-butyraldehyde equivalents or n-butyric acid equivalents, each based on the total moles of n-butyraldehyde equivalents, n-butyric acid equivalents, and n-butanol equivalents.

EXAMPLES

Abbreviations $(MePPh_3)_2CoI_4$=Bis(methyltriphenylphosphonium)cobalt tetraiodide=$(CH_3P(C_6H_5)_3)_2CoI_4$; $(MePBu_3)_2CoI_4$=Bis(methyltributylphosphonium)cobalt tetraiodide=$(CH_3P(C_4H_9)_3)_2CoI_4$; $(MePy)_2CoI_4$=Bis(1-methylpyridinium)cobalt tetraiodide=$(1-CH_3(C_5H_5N))_2CoI_4$; $(MePPh_3)CoBr_4$=Bis(methyltriphenylphosphonium)cobalt tetrabromide=$(CH_3P(C_6H_5)_3)_2CoBr_4$; $CoI_2$=cobalt(II) iodide.

MeI=methyl iodide; DME=dimethyl ether; THF=tetrahydrofuran dppe=1,2-bis(diphenylphosphino)ethane; dppb=1,4-bis(diphenylphosphino)butane; dpph=1,6-bis(diphenylphosphino)hexane: dppbenz=1,2-bis(diphenylphosphino)benzene; bisbi=bis(diphenylphosphinomethyl)biphenyl; $(PPh_2)_3Me$=1,1,1-tris(diphenylphosphino)methane; dppp=1,3-bis(diphenylphosphino)propane; Ph-triphos=1,1,1-tris(diphenylphosphinomethyl)ethane; Et-triphos=1,1,1-tris(diethylphosphinomethyl)ethane; $PPh_3$=triphenylphosphine; bipy=2,2'-bipyridine; P,N=2-(diphenylphosphino)-2'-(N,N-dimethylamino)biphenyl;

$Ru_3(CO)_{12}$=triruthenium dodecacarbonyl; (Ph-triphos)Ru$(CO)_2$=1,1,1-tris(diphenylphosphinomethyl)ethane ruthenium dicarbonyl; $RuO_2xH_2O$=ruthenium(IV)oxide hydrate.

STY=space time yield

For examples having a methanol feed, selectivities are reported as selectivity to acetaldehyde equivalents, acetic acid equivalents, ethanol equivalents, and C4 equivalents relative to methanol carbonylated. Reported acetaldehyde equivalents include: Acetaldehyde, Paraldehyde, Acetaldehyde dimethyl acetal, Acetaldehyde methyl ethyl acetal, Acetaldehyde diethyl acetal. Reported acetic acid equivalents include: Acetic acid, Methyl acetate, and Ethyl acetate. Reported ethanol equivalents include all ethoxy containing products including: Ethanol, Acetaldehyde diethyl acetal, Acetaldehyde methyl ethyl acetal, Diethyl ether, Methyl ethyl ether, and Ethyl acetate. Reported C4 equivalents include: n-Butyl alcohol, Crotonaldehyde, n-Butyraldehyde, Butyraldehyde acetals, and Crotyl alcohol. A summary of commonly observed products and byproducts is provided in Table 1.

TABLE 1 commonly observed products incorporated into selectivity calculations for methanol reductive carbonylation

| Ethanol Equivalents | Acetaldehyde Equivalents | Acetic Acid Equivalents | C4 Equivalents |
|---|---|---|---|
| Ethanol | Acetaldehyde | Acetic acid | n-Butyl alcohol |
| Acetaldehyde diethyl acetal | Acetaldehyde dimethyl acetal | Methyl acetate | Crotonaldehyde |
| Acetaldehyde methyl ethyl acetal | Acetaldehyde methyl ethyl acetal | Ethyl acetate | n-Butyraldehyde |
| Diethyl ether | Acetaldehyde diethyl acetal | | Butyraldehyde acetals |
| Methyl ethyl ether | Paraldehyde | | Crotyl Alcohol |
| Ethyl acetate | | | |

The phosphonium salts and ammonium salts used in these examples are easily prepared by alkylation of the parent tertiary phosphine or amine with an alkyl halide, a process well known to practitioners of the art. Complexes of the type $Y_2CoI_4$ and $Y_2CoBr_4$ where Y=MePPh$_3$ (methyltriphenylphosphonium), Y=MePBu$_3$ (methyltributylphosphonium), Y=MePy (1-methylpyridinium) were prepared by the method of Wegman et al., *J. Mol. Cat.*, 32, (1985), 125-136.

Phosphine ligands, solvents, and alcohols were purchased and used without further processing.

The contents of the examples were analyzed by gas chromatography. When the reaction products formed two liquid phases at room temperature, an additional component, such as THF, was added to ensure a one-phase liquid sample was fed to the gas chromatograph. Catalyst was not removed from the reaction product before analysis. Selectivities are reported based upon detection of the components listed in Table 1. The detection limit for methyl iodide (MeI) was 100 ppm. MeI listed as n/d indicates that no methyl iodide was detected.

Methanol Conversion was calculated as the difference between the initial amount of methanol and the recovered amount of free methanol divided by the initial amount of methanol. Methanol is converted to carbonylated produces and non-carbonylated methoxy-containing products. As the non-carbonylated Methoxy-containing products would be readily recycled in a commercial process, the effective selectivities are based upon the moles of Methanol Carbonylated. The moles of Methanol Carbonylated were calculated as the sum of homologated products.

Moles of Methanol Carbonylated=moles Acetaldehyde+3*moles Paraldehyde+moles Acetaldehyde dimethyl acetal+moles Acetaldehyde methyl ethyl acetal+moles Acetaldehyde diethyl acetal)+moles Acetic acid+moles Methyl acetate+moles Ethyl acetate+moles Ethanol+2*moles Acetaldehyde diethyl acetal+moles Acetaldehyde methyl ethyl acetal+2*moles Diethyl ether+moles Methyl ethyl ether+moles Ethyl acetate+2*moles n-Butyl alcohol+2*moles Crotonaldehyde+2*moles n-Butyraldehyde+2*moles Butyraldehyde acetals+2*moles Crotyl alcohol.

Selectivities to one of the product equivalents, as detailed in equations 1-4 below, are reported as the sum of methanol carbonylated to the product equivalent divided by the total amount of methanol carbonylated.

(1) % Acetaldehyde Equivalents Selectivity=100*(moles Acetaldehyde+3*moles Paraldehyde+moles Acetaldehyde dimethyl acetal+moles Acetaldehyde methyl ethyl acetal+moles Acetaldehyde diethyl acetal)/moles Methanol Carbonylated.

(2) % Acetic Acid Equivalents Selectivity=100*(moles Acetic acid+moles Methyl acetate+moles Ethyl acetate)/moles Methanol Carbonylated (3) % Ethanol Equivalents Selectivity=100*(moles Ethanol+2*moles Acetaldehyde diethyl acetal+moles Acetaldehyde methyl ethyl acetal+2*moles Diethyl ether+moles Methyl ethyl ether+moles Ethyl acetate)/moles Methanol Carbonylated.

(4) % C4 Equivalents Selectivity=100*(2*moles n-Butyl alcohol+2*moles Crotonaldehyde+2*moles n-Butyraldehyde+2*moles Butyraldehyde acetals+2*moles Crotyl alcohol)/moles Methanol Carbonylated.

Yield of Carbonylated Products was calculated as the Moles of Methanol Carbonylated divided by the initial amount of methanol.

Space Time Yield (STY), for a methanol feed and with acetaldehyde equivalents as the desired product, was calculated as the moles of acetaldehyde equivalents produced per liter of initial reaction mixture per hours of reaction (moles per liter per hour, $Mh^{-1}$). One skilled in the art can readily calculate the STY when ethanol equivalents are the desired product.

Mole percent (Mole %) of methyl iodide (MeI) or dimethyl ether (DME) were calculated as the percentage of moles of species produced compared to the initial amount of methanol (or other alcohol) charged to the reactor.

Example 1

A 100-mL Hastelloy® C autoclave was charged with a solution of $(MePPh_3)_2CoI_4$ (1.236 mmol) in 25 mL of methanol, sealed and purged 3 times with $N_2$. The reactor was pressurized to 6.9 MPa (1000 psig) with 1:1 CO:$H_2$ and heated to 190° C. Upon reaching 190° C., the reactor was pressurized to a total pressure of 27.6 MPa (4000 psig) with 1:1 CO:$H_2$. After 30 minutes the reactor was cooled to 5° C.

and the gas was vented. The contents were analyzed by gas chromatography and the results are shown in Table 2.

Examples 2-6 and Comparative Example C1

Example 1 was repeated except the catalyst used and the amount of catalyst were as given in Table 2. Example 2 is a duplicate of Example 1 with the other examples varying the amount and/or type of catalyst. While Comparative Example C1 shows a Space Time Yield comparable to Examples 1-6, the crude reductive carbonylation product contains 0.23 mole % methyl iodide and 3.4 mole % dimethyl ether, each based on the amount of methanol charged. Examples 1-6 show no detectable methyl iodide and 0.8 mole % as the highest level of DME.

Examples 7-14 and Comparative Examples C2-05

Example 1 was repeated with the addition of a solvent used at a 50 vol % level. The solvent used and the amount of catalyst, as well as the results, are given in Table 2. One skilled in the art would recognize that the Space Time Yield would be lower for systems with 50 vol % solvent compared to systems with no solvent. For example, comparing Examples 1 and 7 which were run under the same conditions except that Example 7 had 50 vol % toluene, the STY for Example 1 was 13.8 while the STY for Example 7 was 8.4. The use of solvent does, however, improve selectivity to acetaldehyde equivalents. For Example 7, the selectivity to acetaldehyde equivalents was 89% compared to 74% for Example 1. Each of Examples 7-14 produced products which separated into two distinct liquid phases at room temperature. Advantageously, the catalyst, which would be recycled in a continuous process, partitioned to the aqueous phase, while the desired products partitioned to the organic phase (see Examples 87-90). Comparative Examples C2-05 did not form two distinct liquid phases at room temperature. Furthermore, Comparative Example C5, with acetonitrile as the solvent, showed the lowest STY of 4.8.

TABLE 2

Reductive carbonylation of methanol to acetaldehyde equivalents at 190° C., 4000 psig, carbon monoxide to hydrogen ratio of 1:1 for 30 minutes.

| Ex | Catalyst | Catalyst Conc. (mole % relative to Methanol) | Solvent | Methanol Conversion | Yield of Carbonylated Products |
|---|---|---|---|---|---|
| 1 | (MePPh3)2CoI4 | 0.2% | — | 75% | 38% |
| 2 | (MePPh3)2CoI4 | 0.2% | — | 73% | 40% |
| 3 | (MePPh3)2CoI4 | 0.4% | — | 77% | 47% |
| 4 | (MePPh3)2CoI4 | 0.025% | — | 55% | 19% |
| 5 | (MePBu3)2CoI4 | 0.2% | — | 71% | 36% |
| 6 | (MePy)2CoI4 | 0.2% | — | 72% | 37% |
| C1 | CoI2 / MeI | 0.2% / 0.4% | — | 69% | 26% |
| 7 | (MePPh3)2CoI4 | 0.2% | Toluene | 83% | 38% |
| 8 | (MePPh3)2CoI4 | 0.4% | Toluene | 81% | 47% |
| 9 | (MePPh3)2CoI4 | 0.4% | Heptane | 80% | 38% |
| 10 | (MePPh3)2CoI4 | 0.2% | Cyclohexane | 78% | 33% |
| 11 | (MePPh3)2CoI4 | 0.4% | Ethylbenzene | 83% | 47% |
| 12 | (MePPh3)2CoI4 | 0.2% | Diethyl ether | 70% | 32% |
| 13 | (MePPh3)2CoI4 | 0.4% | Diethyl ether | 80% | 43% |
| 14 | (MePPh3)2CoI4 | 0.4% | 4-Methylanisole | 83% | 53% |
| C2 | (MePPh3)2CoI4 | 0.4% | THF | 83% | 54% |
| C3 | (MePPh3)2CoI4 | 0.4% | Dioxane | 78% | 55% |
| C4 | (MePPh3)2CoI4 | 0.2% | Acetone | 74% | 42% |
| C5 | (MePPh3)2CoI4 | 0.2% | Acetonitrile | 62% | 25% |

| Ex | Acetaldehyde Selectivity | Ethanol Selectivity | Acetic Acid Selectivity | C4 Selectivity | STY ($Mh^{-1}$) | Mole % MeI in product | Mole % DME in product |
|---|---|---|---|---|---|---|---|
| 1 | 74% | 2% | 15% | 9% | 13.8 | n/d | 0.5% |
| 2 | 73% | 2% | 15% | 10% | 14.5 | n/d | 0.6% |
| 3 | 65% | 2% | 20% | 13% | 15.3 | n/d | 0.8% |
| 4 | 88% | 3% | 7% | 2% | 8.4 | n/d | 0.5% |
| 5 | 76% | 2% | 12% | 10% | 13.4 | n/d | 0.6% |
| 6 | 72% | 2% | 13% | 13% | 13.2 | n/d | 0.7% |
| C1 | 79% | 2% | 9% | 10% | 10.2 | 0.23% | 3.4% |
| 7 | 89% | 4% | 5% | 2% | 8.4 | n/d | 0.3% |
| 8 | 86% | 3% | 7% | 4% | 9.8 | n/d | 0.3% |
| 9 | 79% | 2% | 16% | 3% | 5.4 | n/d | 0.2% |
| 10 | 88% | 5% | 4% | 2% | 7.2 | n/d | 0.2% |
| 11 | 86% | 2% | 8% | 3% | 10 | n/d | 0.3% |
| 12 | 86% | 5% | 6% | 2% | 6.8 | n/d | 0.2% |
| 13 | 78% | 5% | 13% | 4% | 8.25 | n/d | 0.2% |
| 14 | 81% | 2% | 10% | 7% | 10.5 | n/d | 0.4% |
| C2 | 77% | 2% | 14% | 7% | 10.3 | n/d | 0.2% |
| C3 | 82% | 2% | 13% | 3% | 11.1 | n/d | 0.3% |
| C4 | 84% | 2% | 9% | 5% | 8.7 | n/d | 0.3% |
| C5 | 76% | 3% | 15% | 6% | 4.8 | n/d | 0.2% |

The results of Example 9, with heptane as the solvent, show an unexpectedly low STY compared to other solvent examples with the $(MePPh_3)_2CoI_4$ catalyst level of 0.4 mole % (e.g., Examples 8, 11, 13, and 14). This is believed to be an anomaly of the analysis, as this was the only Example in which each of the two liquid phases was analyzed separately.

Example 15

Example 1 was repeated at a temperature of 195° C. and 0.025 mole % $(MePPh_3)_2CoI_4$ catalyst as shown with the corresponding results in Table 3.

Comparative Examples C6-C8

Example 15 was repeated using the same total amount of catalyst, but varying the relative amounts of $(MePPh_3)_2CoI_4$ and $(MePPh_3)_2CoBr_4$ as given in Table 3. At the same total catalyst concentration, the Space Time Yield decreased from 9.8 with all $(MePPh_3)_2CoI_4$ (Example 15) down to 2.5 with all $(MePPh_3)_2CoBr_4$ (Comparative Example C8). These examples show that an iodide cation for catalyzing the reductive carbonylation of methanol to acetaldehyde equivalents produces a higher STY than a bromide cation.

Example 16

Example 1 was repeated at a temperature of 195° C. and 0.2 mole % $(MePPh_3)_2CoI_4$ catalyst as shown with the corresponding results in Table 3.

Examples 17-26

Example 16 was repeated with the amount of $(MePPh_3)_2CoI_4$ catalyst shown and varying amounts of phosphine ligand, 1,3-bis(diphenylphosphino)propane (dppp), as shown in Table 3. The amount of phosphine ligand is given in mole % phosphine ligand relative to the initial amount of methanol. Examples 25 and 26 were run for 1 hour. Results are shown in Table 3.

Examples 27-31

Example 16 was repeated with 50 vol % toluene as a solvent and the amounts of $(MePPh_3)_2CoI_4$ and dppp as shown in Table 3. Examples 27 and 28 were run for one hour. The contents were analyzed by gas chromatography and the results are shown in Table 3.

Examples 16, 17, and 29 were each run at 195° C., 4000 psig, $CO:H_2$ of 1:1, and 0.2 mole % $(MePPh_3)_2CoI_4$ for 30 min. The STY increased from 11.8 with no phosphine ligand present (Example 16) to 16.4 with 0.1 mole % dppp present (Example 17). Comparison of the selectivity to acetaldehyde equivalents shows that the addition of a toluene solvent gave an acetaldehyde equivalents selectivity of 84% (Example 29) which is higher than the catalyst alone or catalyst with phosphine ligand values of 73% (Example 16) and 63% (Example 17), respectively.

TABLE 3

Reductive carbonylation of methanol to acetaldehyde equivalents at 195° C., 4000 psig, carbon monoxide to hydrogen ratio of 1:1 for 30 minutes.

| Ex | Time | Catalyst | Catalyst Conc. (mole % relative to Methanol) | Phosphine ligand | Solvent |
|---|---|---|---|---|---|
| 15 | 0.5 | (MePPh3)2CoI4 | 0.025% | — | — |
| C6 | 0.5 | (MePPh3)2CoI4 | 0.0125% | — | — |
|  |  | (MePPh3)2CoBr4 | 0.0125% |  |  |
| C7 | 0.5 | (MePPh3)2CoI4 | 0.00625% | — | — |
|  |  | (MePPh3)2CoBr4 | 0.01875% |  |  |
| C8 | 0.5 | (MePPh3)2CoBr4 | 0.025% | — | — |
| 16 | 0.5 | (MePPh3)2CoI4 | 0.2% | — | — |
| 17 | 0.5 | (MePPh3)2CoI4 | 0.2% | dppp(0.1%) | — |
| 18 | 0.5 | (MePPh3)2CoI4 | 0.4% | dppp(0.2%) | — |
| 19 | 0.5 | (MePPh3)2CoI4 | 0.6% | dppp(0.3%) | — |
| 20 | 0.5 | (MePPh3)2CoI4 | 0.2% | Et-tripohs(0.1%) | — |
| 21 | 0.5 | (MePPh3)2CoI4 | 0.2% | Et-tripohs(0.2%) | — |
| 22 | 0.5 | (MePPh3)2CoI4 | 0.2% | Et-tripohs(0.3%) | — |
| 23 | 0.5 | (MePPh3)2CoI4 | 0.2% | Et-tripohs(0.4%) | — |
| 24 | 0.5 | (MePPh3)2CoI4 | 0.4% | Et-tripohs(0.2%) | — |
| 25 | 1 | (MePPh3)2CoI4 | 0.4% | dppp(0.2%) | — |
| 26 | 1 | (MePPh3)2CoI4 | 0.6% | dppp(0.3%) | — |
| 27 | 1 | (MePPh3)2CoI4 | 0.4% | dppp(0.2%) | Toluene |
| 28 | 1 | (MePPh3)2CoI4 | 0.6% | dppp(0.3%) | Toluene |
| 29 | 0.5 | (MePPh3)2CoI4 | 0.2% | dppp(0.1%) | Toluene |
| 30 | 0.5 | (MePPh3)2CoI4 | 0.4% | dppp(0.2%) | Toluene |
| 31 | 0.5 | (MePPh3)2CoI4 | 0.6% | dppp(0.3%) | Toluene |

| Ex | Methanol Conversion | Yield of Carbonylated Products | Acetaldehyde Selectivity | Ethanol Selectivity | Acetic Acid Selectivity | C4 Selectivity | Space Time Yield (Mh$^{-1}$) |
|---|---|---|---|---|---|---|---|
| 15 | 67% | 24% | 83% | 6% | 8% | 3% | 9.8 |
| C6 | 39% | 13% | 86% | 3% | 8% | 3% | 5.4 |
| C7 | 35% | 10% | 87% | 2% | 8% | 3% | 4.1 |
| C8 | 34% | 6% | 86% | 2% | 8% | 4% | 2.5 |
| 16 | 68% | 33% | 73% | 3% | 16% | 8% | 11.8 |
| 17 | 76% | 53% | 63% | 9% | 18% | 10% | 16.4 |
| 18 | 89% | 49% | 58% | 10% | 21% | 11% | 14.1 |
| 19 | 94% | 62% | 41% | 14% | 28% | 17% | 12.7 |

TABLE 3-continued

Reductive carbonylation of methanol to acetaldehyde equivalents at 195° C., 4000 psig, carbon monoxide to hydrogen ratio of 1:1 for 30 minutes.

| | | | | | | | |
|---|---|---|---|---|---|---|---|
| 20 | 78% | 51% | 72% | 4% | 16% | 8% | 18.2 |
| 21 | 83% | 57% | 72% | 4% | 17% | 7% | 20.1 |
| 22 | 79% | 48% | 76% | 3% | 17% | 4% | 17.9 |
| 23 | 30% | 10% | 79% | 0.8% | 17% | 3% | 3.7 |
| 24 | 90% | 62% | 65% | 4% | 22% | 9% | 19.8 |
| 25 | 95% | 64% | 45% | 15% | 23% | 17% | 7.2 |
| 26 | 95% | 64% | 33% | 10% | 39% | 18% | 5.2 |
| 27 | 93% | 72% | 71% | 7% | 11% | 11% | 6.3 |
| 28 | 96% | 66% | 56% | 8% | 17% | 19% | 4.6 |
| 29 | 82% | 42% | 84% | 4% | 10% | 2% | 8.6 |
| 30 | 86% | 52% | 80% | 5% | 10% | 5% | 10.3 |
| 31 | 94% | 66% | 64% | 6% | 14% | 15% | 10.3 |

The Examples and Comparative Examples of Table 3 each showed no detectable amount of MeI. The amount of DME ranged from 0.3 mole % to 0.8 mole % for Examples 15-19 and 25-31 and from 0.4 mole % to 1.9 mole % for Examples 20-24.

Examples 32-42

Example 1 was repeated at the temperature, carbon monoxide to hydrogen ratio, dppp at 0.1 mole % if present, and toluene at 50 vol % if present as shown in Table 4. All examples had 0.2 mole % $(MePPh_3)_2CoI_4$ as the catalyst except for example 42 which had 0.4 mole %.

Selectivity to acetaldehyde equivalents improved as the ratio of carbon monoxide to hydrogen went from 2:1 to 1:1 to 1:2. Examples 36, 17, and 37 were each run at a temperature of 195° C., 4000 psig, 0.2 mole % $(MePPh_3)_2CoI_4$ and 0.1 mole % dppp. These Examples show that acetaldehyde equivalents selectivities increased from 48% (Example 36, $CO:H_2$ of 2:1) to 63% (Example 17, $CO:H_2$ of 1:1) to 70% (Example 37 $CO:H_2$ of 1:2).

The Examples of Table 4 each showed no detectable amount of MeI. The amount of DME ranged from 0.2 mole % to 0.8 mole % for Examples 32-39 and from 0.6 mole % to 1.8 mole % for Examples 40-42, based on the initial amount of methanol charged. Examples 42 was run with 0.4 mole % $(MePPh_3)_2CoI_4$.

Examples 43a-43c

This Example illustrates the effect of recycling the cobalt catalyst. For Example 43a, Example 1 was repeated at a temperature of 175° C., pressure of 2400 psig, and 0.05 mole % $(MePPh_3)_2CoI_4$ as the catalyst. A total amount of 60 mL methanol was charged. The contents were analyzed by gas chromatography. The catalyst was recovered for recycling by removing volatiles from the reaction mixture by rotary evaporation, leaving a green crystalline solid. For Example 43b, the solid catalyst was dissolved in enough methanol to maintain 0.05 mole % $(MePPh_3)_2CoI_4$ catalyst concentration. Example 43b was run under the same conditions as Example 43a. For Example 43c, volatiles were again

TABLE 4

Reductive carbonylation of methanol to acetaldehyde equivalents at 4000 psig and 0.2 mole % $(MePPh_3)_2CoI_4$ for 30 minutes.

| Ex | Temp. C. ° | $CO:H_2$ | Phosphine ligand | Solvent |
|---|---|---|---|---|
| 32 | 190 | 2:1 | — | — |
| 33 | 190 | 1:2 | — | — |
| 34 | 190 | 2:1 | — | Toluene |
| 35 | 190 | 1:2 | — | Toluene |
| 36 | 195 | 2:1 | dppp(0.1%) | — |
| 37 | 195 | 1:2 | dppp(0.1%) | — |
| 38 | 195 | 2:1 | dppp(0.1%) | Toluene |
| 39 | 195 | 1:2 | dppp(0.1%) | Toluene |
| 40 | 195 | 1:2 | Et-tripohs(0.1%) | — |
| 41 | 195 | 1:2 | Et-tripohs(0.2%) | — |
| 42 | 195 | 1:2 | Et-tripohs(0.2%) | — |

| Ex | Methanol Conversion | Yield of Carbonylated Products | Acetaldehyde Selectivity | Ethanol Selectivity | Acetic Acid Selectivity | C4 Selectivity | Space Time Yield (Mh$^{-1}$) |
|---|---|---|---|---|---|---|---|
| 32 | 78% | 45% | 66% | 1% | 28% | 5% | 14.5 |
| 33 | 61% | 25% | 84% | 3% | 7% | 6% | 10.2 |
| 34 | 83% | 35% | 81% | 1% | 16% | 2% | 7 |
| 35 | 65% | 22% | 91% | 4% | 3% | 2% | 5 |
| 36 | 87% | 55% | 48% | 3% | 43% | 6% | 12.9 |
| 37 | 78% | 33% | 70% | 14% | 7% | 9% | 11.6 |
| 38 | 77% | 31% | 72% | 3% | 20% | 5% | 5.5 |
| 39 | 70% | 23% | 89% | 4% | 4% | 3% | 5 |
| 40 | 79% | 28% | 79% | 6% | 6% | 9% | 11.1 |
| 41 | 88% | 35% | 81% | 8% | 6% | 5% | 14.0 |
| 42 | 83% | 40% | 73% | 9% | 8% | 10% | 14.6 | removed by rotary evaporation and the green crystalline solid was again dissolved in enough methanol to maintain 0.05 mole % (MePPh$_3$)$_2$CoI$_4$ catalyst concentration. The solution was then run under the same conditions as Example 43a. Results are shown in Table 5. Comparison of Examples 43a-43c show similar values for methanol conversion, acetaldehyde equivalents selectivity, and STY after the (MePPh$_3$)$_2$CoI$_4$ catalyst was recycled a first and second time.

Examples 44-52 and Comparative Examples C9 and C10

For Examples 44 and 45, Example 1 was repeated at a temperature of 175° C. and a pressure of 2400 psig. Examples 46-52 and Comparative Examples C9 and 010 repeated Example 44 with 0.1 mole % of the phosphine ligand listed in Table 5. The STY for Examples 44 and 45, which had no phosphine ligand, were 6.7 and 7.8, respectively. The STY for Examples 46-52, which had inventive catalyst/phosphine ligand combinations ranged from 7.6-11.0. The STY for Comparative Examples C9 and 010 was 5.4 and 7.5, respectively.

Examples 53-57 and Comparative Examples C11-013

Example 53 repeated Example 1 at a temperature of 190° C. and a pressure of 2400 psig. Examples 54-57 and Comparative Examples C11-C13 repeated Example 53 with 0.1 mole % of the phosphine ligand listed in Table 5. The STY for Example 53, which had no phosphine ligand, was 6.0. The STY for Examples 54-57, which had inventive catalyst/phosphine ligand combinations ranged from 9.4-11.2. The STY for Comparative Example C11 and C12 which did not have an inventive catalyst/phosphine ligand combination was 8.9 and 6.9, respectively. Comparative Example C13 repeated Example 53 using a catalyst of 0.2 mole % CoI$_2$ and 0.2 mole % MeI with 0.1 mole % dppp in place of the 0.2 mole % (MePPh$_3$)$_2$CoI$_4$ with 0.1 mole % dppp for the catalyst/phosphine ligand combination. Comparative Example C13 had a STY of 10.2, but also had 0.08 mole % MeI and 1.4 mole % DME in the crude reductive carbonylation product as compared to non-detectable MeI and 0.7 mole % DME for Example 53.

TABLE 5

Reductive carbonylation of methanol to acetaldehyde equivalents at 2400 psig a carbon monoxide to hydrogen ratio of 1:1 for 30 minutes.

| Ex. | Temp C. ° | Catalyst | Catalyst Conc. (mole % relative to Methanol) | Phosphine ligand | Methanol Conversion | Yield of Carbonylated Products |
|---|---|---|---|---|---|---|
| 43a | 175 | (MePPh3)2CoI4 | 0.05% | — | 37% | 11% |
| 43b | 175 | (MePPh3)2CoI4 | 0.05% | — | 36% | 11% |
| 43c | 175 | (MePPh3)2CoI4 | 0.05% | — | 43% | 11% |
| 44 | 175 | (MePPh3)2CoI4 | 0.2% | — | 50% | 17% |
| 45 | 175 | (MePPh3)2CoI4 | 0.2% | — | 53% | 20% |
| 46 | 175 | (MePPh3)2CoI4 | 0.2% | dppp(0.1%) | 72% | 30% |
| 47 | 175 | (MePPh3)2CoI4 | 0.2% | dppp(0.1%) | 73% | 31% |
| 48 | 175 | (MePPh3)2CoI4 | 0.2% | Ph-triphos(0.1%) | 64% | 23% |
| 49 | 175 | (MePPh3)2CoI4 | 0.2% | Ph-triphos(0.1%) | 62% | 25% |
| 50 | 175 | (MePPh3)2CoI4 | 0.2% | bisbi(0.1%) | 61% | 25% |
| 51 | 175 | (MePPh3)2CoI4 | 0.2% | dpph(0.1%) | 55% | 20% |
| 52 | 175 | (MePPh3)2CoI4 | 0.2% | dppb(0.1%) | 56% | 19% |
| C9 | 175 | (MePPh3)2CoI4 | 0.2% | bipy(0.1%) | 41% | 14% |
| C10 | 175 | (MePPh3)2CoI4 | 0.2% | P,N(0.1%) | 57% | 19% |
| 53 | 190 | (MePPh3)2CoI4 | 0.2% | — | 45% | 14% |
| 54 | 190 | (MePPh3)2CoI4 | 0.2% | dppp(0.1%) | 70% | 32% |
| 55 | 190 | (MePPh3)2CoI4 | 0.2% | dppe(0.1%) | 66% | 26% |
| 56 | 190 | (MePPh3)2CoI4 | 0.2% | dppbenz(0.1%) | 70% | 31% |
| 57 | 190 | (MePPh3)2CoI4 | 0.2% | Ph-triphos(0.1%) | 62% | 25% |
| C11 | 190 | (MePPh3)2CoI4 | 0.2% | (PPh2)3Me (0.1%) | 59% | 23% |
| C12 | 190 | (MePPh3)2CoI4 | 0.2% | PPh3(0.2%) | 53% | 18% |
| C13 | 190 | CoI2 MeI | 0.2% 0.2% | dppp(0.1%) | 69% | 27% |

| Ex. | Acetaldehyde Selectivity | Ethanol Selectivity | Acetic Acid Selectivity | C4 Selectivity | Space Time Yield (Mh$^{-1}$) | Mole % MeI in Product | Mole % DME in Product |
|---|---|---|---|---|---|---|---|
| 43a | 88% | 1% | 11% | 0% | 4.7 | n/d | 0.4% |
| 43b | 83% | 1% | 12% | 4% | 4.4 | n/d | 0.3% |
| 43c | 85% | 1% | 14% | 0% | 4.5 | n/d | 0.3% |
| 44 | 80% | 1% | 18% | 1% | 6.7 | n/d | 0.3% |
| 45 | 78% | 1% | 19% | 2% | 7.8 | n/d | 0.5% |
| 46 | 73% | 4% | 20% | 3% | 10.7 | n/d | 0.6% |
| 47 | 72% | 4% | 20% | 3% | 11.0 | n/d | 0.6% |
| 48 | 77% | 2% | 19% | 2% | 8.8 | n/d | 0.4% |
| 49 | 77% | 2% | 19% | 2% | 9.7 | n/d | 0.4% |
| 50 | 78% | 3% | 16% | 4% | 9.4 | n/d | 0.3% |
| 51 | 79% | 2% | 16% | 2% | 7.8 | n/d | 0.2% |
| 52 | 80% | 3% | 16% | 2% | 7.6 | n/d | 0.2% |
| C9 | 80% | 1% | 19% | 1% | 5.4 | n/d | 0.3% |
| C10 | 77% | 1% | 21% | 1% | 7.3 | n/d | 0.2% |
| 53 | 84% | 1% | 14% | 1% | 6.0 | n/d | 0.7% |

TABLE 5-continued

Reductive carbonylation of methanol to acetaldehyde equivalents at 2400 psig a carbon monoxide to hydrogen ratio of 1:1 for 30 minutes.

| 54 | 71% | 4% | 20% | 4% | 11.1 | n/d | 0.7% |
|---|---|---|---|---|---|---|---|
| 55 | 74% | 3% | 21% | 2% | 9.4 | n/d | 0.5% |
| 56 | 72% | 5% | 20% | 2% | 11.2 | n/d | 0.7% |
| 57 | 77% | 2% | 19% | 2% | 9.7 | n/d | 0.4% |
| C11 | 77% | 1% | 19% | 2% | 8.9 | n/d | 0.5% |
| C12 | 78% | 1% | 19% | 2% | 6.9 | n/d | 0.2% |
| C13 | 76% | 3% | 17% | 4% | 10.2 | 0.08% | 1.4% |

Examples 58-61

For Example 58, a 100-mL Hastelloy® C autoclave was charged with a solution of $(MePPh_3)_2CoI_4$ (1.34 mmol) in 25 mL of n-propanol. The autoclave was sealed and purged 3 times with nitrogen. The reactor was pressurized to 6.9 MPa (1000 psig) with 1:1 $CO:H_2$ and heated to 195° C. Upon reaching the desired temperature, the reactor was pressurized to a total pressure of 27.6 MPa (4000 psig) with 1:1 $CO:H_2$. After 30 minutes the reactor was cooled to 5° C. and the gas was vented. The contents were analyzed by gas chromatography and the amount of n-butyraldehyde produced is shown in Table 6. Examples 59-61 were run at the conditions shown in Table 6 and show the production of n-butyraldehyde by the reductive carbonylation of n-propanol. Table 6 shows weight percent of n-butyraldehyde in the crude reductive carbonylation product; it does not include any other components that could be an n-butyraldehyde equivalents.

TABLE 6 reductive carbonylation of n-propanol to n-butyraldehyde at 195° C., 4000 psig and a carbon monoxide to hydrogen ratio of 1:1

| Ex. | Time (hr) | Catalyst | Catalyst Conc. (mole % relative to n-propanol) | Phosphine ligand | Wt % n-butyr-aldehyde |
|---|---|---|---|---|---|
| 58 | 0.5 | (MePPh3)2CoI4 | 0.2% | — | 1.4% |
| 59 | 1 | (MePPh3)2CoI4 | 0.2% | — | 2.6% |
| 60 | 0.5 | (MePPh3)2CoI4 | 0.2% | dppp (0.1%) | 1.4% |
| 61 | 1 | (MePPh3)2CoI4 | 0.2% | dppp (0.1%) | 3.0% |

Examples 62-77 and C14-C15

These examples illustrate the ability to selectively produce ethanol equivalents with the use of a ruthenium co-catalyst. For Example 62, a 100-mL Hastelloy® C autoclave was charged with a solution of $(MePPh_3)_2CoI_4$ (1.236 mmol), dppp (0.618 mmol), and $Ru_3(CO)_{12}$ (0.206 mmol) in 25 mL of methanol. The autoclave was sealed and purged 3 times with nitrogen. The reactor was pressurized to 6.9 MPa (1000 psig) with 1:1 CO: $H_2$ and heated to 195° C. Upon reaching the desired temperature, the reactor was pressurized to a total pressure of 16.5 MPa (2400 psig) with 1:1 CO: $H_2$. After 30 minutes the reactor was cooled to 5° C. and the gas was vented. The contents were analyzed by gas chromatography. The results are given in Table 7. Examples 63-77 and Comparative Examples C14 and C15 repeated Example 62 at the conditions shown in Table 7; all runs were conducted with a CO:H2 ratio of 1:1 and for 30 minutes, except Example 75 was conducted for one hour. If toluene was present, it was present at 50 vol. %. No methyl iodide was detected in any of the crude reductive carbonylation products listed in Table 7.

TABLE 7 reductive carbonylation of methanol to ethanol with $CO:H_2$ 1:1 for 30 min.

| Ex. | Temp. C. | Pres. (psig) | Catalyst | catalyst conc. (mol % relative to Methanol) | ligand | solvent |
|---|---|---|---|---|---|---|
| 62 | 195 | 2400 | (MePPh3)2CoI4 Ru3(CO)12 | 0.2% 0.03% | dppp (0.1%) | — |
| 63 | 195 | 2400 | (MePPh3)2CoI4 Ru3(CO)12 | 0.2% 0.03% | dppp (0.2%) | — |
| 64 | 195 | 2400 | (MePPh3)2CoI4 Ru3(CO)12 | 0.2% 0.07% | — | — |
| 65 | 195 | 2400 | (MePPh3)2CoI4 Ru3(CO)12 | 0.2% 0.07% | dppp (0.1%) | — |
| 66 | 195 | 2400 | (MePPh3)2CoI4 Ru3(CO)12 | 0.2% 0.07% | Ph-triphos (0.1%) | — |
| 67 | 190 | 4000 | (MePPh3)2CoI4 Ru3(CO)12 | 0.4% 0.133% | — | — |
| 68 | 190 | 4000 | (MePPh3)2CoI4 Ru3(CO)12 | 0.4% 0.133% | dppp (0.2%) | — |

TABLE 7-continued reductive carbonylation of methanol to ethanol with CO:H$_2$ 1:1 for 30 min.

| Ex. | Temp | Press | Catalyst | conc. | ligand | solvent |
|---|---|---|---|---|---|---|
| 69 | 190 | 4000 | (MePPh3)2CoI4 | 0.4% | — | Toluene |
|    |     |      | Ru3(CO)12 | 0.133% | | |
| 70 | 195 | 4000 | (MePPh3)2CoI4 | 0.2% | | — |
|    |     |      | Ru3(CO)12 | 0.07% | | |
| 71 | 195 | 4000 | (MePPh3)2CoI4 | 0.2% | dppp | — |
|    |     |      | Ru3(CO)12 | 0.07% | (0.1%) | |
| 72 | 195 | 4000 | (MePPh3)2CoI4 | 0.2% | Ph-triphos | — |
|    |     |      | Ru3(CO)12 | 0.07% | (0.1%) | |
| 73 | 195 | 4000 | (MePPh3)2CoI4 | 0.4% | dppp | — |
|    |     |      | Ru3(CO)12 | 0.133% | (0.2%) | |
| 74 | 195 | 4000 | (MePPh3)2CoI4 | 0.4% | dppp | |
|    |     |      | Ru3(CO)12 | 0.133% | (0.2%) | |
| 75 | 195 | 4000 | (MePPh3)2CoI4 | 0.4% | dppp | |
|    |     |      | Ru3(CO)12 | 0.133% | (0.2%) | |
| 76 | 195 | 4000 | (MePPh3)2CoI4 | 0.4% | dppp | |
|    |     |      | (Ph-Triphos)Ru(CO)2 | 0.2% | (0.2%) | |
| 77 | 195 | 4000 | (MePPh3)2CoI4 | 0.4% | dppp | Toluene |
|    |     |      | (Ph-Triphos)Ru(CO)2 | 0.2% | (0.2%) | |
| C14 | 175 | 4000 | CoI2 | 0.2% | dppp | — |
|    |     |      | MeI | 0.2% | (0.1%) | |
|    |     |      | Ru3(CO)12 | 0.07% | | |
| C15 | 175 | 4000 | CoI2 | 0.2% | dppp | — |
|    |     |      | MeI | 0.2% | (0.1%) | |
|    |     |      | Ru3(CO)12 | 0.07% | | |

| Ex. | Methanol Conversion | Yield of Carbonylated Products | Acetaldehyde selectivity | Ethanol Selectivity | Acetyls Selectivity | C4 Selectivity | Space Time Yield (Mh$^{-1}$) | Mol % DME in product |
|---|---|---|---|---|---|---|---|---|
| 62 | 39% | 15% | 23% | 62% | 13% | 3% | 4.2 | 0.2% |
| 63 | 38% | 14% | 54% | 33% | 9% | 4% | 2.2 | 0.2% |
| 64 | 24% | 10% | 7% | 76% | 13% | 4% | 2.3 | 0.1% |
| 65 | 28% | 11% | 7% | 75% | 15% | 4% | 3.2 | 0.1% |
| 66 | 28% | 10% | 7% | 75% | 13% | 5% | 7.7 | 0.1% |
| 67 | 70% | 43% | 8% | 68% | 21% | 3% | 13.0 | 0.2% |
| 68 | 64% | 38% | 5% | 74% | 20% | 1% | 12.2 | 0.3% |
| 69 | 55% | 20% | 16% | 75% | 8% | 1% | 3.6 | 0.0% |
| 70 | 43% | 24% | 2% | 88% | 8% | 2% | 8.2 | 0.3% |
| 71 | 44% | 25% | 4% | 85% | 10% | 2% | 8.7 | 0.2% |
| 72 | 38% | 22% | 4% | 87% | 8% | 2% | 7.7 | 0.2% |
| 73 | 58% | 33% | 4% | 85% | 11% | 1% | 12.4 | 0.2% |
| 74 | 48% | 27% | 3% | 90% | 7% | 1% | 10.5 | 0.2% |
| 75 | 57% | 36% | 2% | 92% | 6% | 1% | 7.2 | 0.3% |
| 76 | 76% | 40% | 45% | 41% | 8% | 6% | 7.7 | 0.3% |
| 77 | 75% | 40% | 45% | 43% | 7% | 6% | 4.0 | 0.4% |
| C14 | 48% | 28% | 4% | 82% | 14% | 0% | 9.6 | 0.8% |
| C15 | 52% | 31% | 4% | 82% | 14% | 0% | 10.3 | 1.1% |

All Examples were conducted for 30 minutes except Example 75 was conducted for one hour.

Examples 78-83

For Example 78, Example 67 was repeated with a carbon monoxide to hydrogen (CO:H$_2$) ratio of 1:2. The contents were analyzed by gas chromatography. Results are given in Table 8. Examples 79-83 repeated Example 78 at the conditions noted in Table 8. All of the Examples in Table 8 were conducted at 4000 psig and CO:H$_2$ ratio of 1:2.

TABLE 8 reductive carbonylation of methanol to ethanol at 4000 psig and a CO:H$_2$ of 1:2

| Ex. | Temp. C. | Time (h) | Catalyst | catalyst conc. (mol % relative to Methanol) | ligand | solvent |
|---|---|---|---|---|---|---|
| 78 | 190 | 0.5 | (MePPh3)2CoI4 | 0.4% | — | — |
|    |     |     | Ru3(CO)12 | 0.133% | | |
| 79 | 195 | 0.5 | (MePPh3)2CoI4 | 0.4% | dppp | Toluene |
|    |     |     | Ru3(CO)12 | 0.133% | (0.2%) | |

TABLE 8-continued reductive carbonylation of methanol to ethanol at 4000 psig and a $CO:H_2$ of 1:2

| | | | | | | |
|---|---|---|---|---|---|---|
| 80 | 195 | 1 | (MePPh3)2CoI4 | 0.4% | dppp | Toluene |
| | | | Ru3(CO)12 | 0.133% | (0.2%) | |
| 81 | 195 | 0.5 | (MePPh3)2CoI4 | 0.6% | dppp | |
| | | | Ru3(CO)12 | 0.2% | (0.3%) | |
| 82 | 195 | 0.5 | (MePPh3)2CoI4 | 0.4% | | |
| | | | RuO2•xH2O | 0.019% | | |
| 83 | 195 | 2 | (MePPh3)2CoI4 | 0.4% | | |
| | | | RuO2•xH2O | 0.019% | | |

| Ex. | Methanol Conversion | Yield of Carbonylated Products | Acetaldehyde selectivity | Ethanol Selectivity | Acetyls Selectivity | C4 Selectivity | Space Time Yield ($Mh^{-1}$) | Mol % DME in product |
|---|---|---|---|---|---|---|---|---|
| 78 | 44% | 28% | 1% | 91% | 8% | 0% | 10.3 | 0.3% |
| 79 | 33% | 16% | 9% | 78% | 7% | 6% | 2.6 | 0.1% |
| 80 | 41% | 29% | 5% | 87% | 5% | 4% | 2.7 | 0.1% |
| 81 | 61% | 34% | 3% | 86% | 9% | 3% | 12.4 | 0.2% |
| 82 | 33% | 9% | 23% | 60% | 13% | 4% | 2.0 | 0.5% |
| 83 | 51% | 28% | 5% | 87% | 7% | 1% | 2.6 | 1.1% |

Examples 84-87

The reductive carbonylation reaction of Example 1 was repeated twice using 0.4 mole % $(MePPh_3)_2CoI_4$ and 50 vol % toluene. The cooled reductive carbonylation product for Examples 84 and 86 partitioned into two layers. The relative partitioning of selected components are given in Tables 9 (organics) and 10 (catalyst). The reductive carbonylation of Example 1 was again repeated twice using 0.4 mole % $(MePPh_3)_2CoI_4$ and 50 vol % hexane. The cooled reductive carbonylation products for Examples 85 and 87 partitioned into two layers. The relative partitioning of selected components are given in Tables 9 and 10. The results shown in Table 9, the partitioning of the organic compounds, were calculated based upon gas chromatography analysis. The partitioning of the catalyst component was determined using XRF. One skilled in the art, based on these preliminary results, can expect that the desired products could be extracted using a non-polar solvent, such as toluene, while the catalyst would remain in the polar phase and be readily recycled to the carbonylation reactor.

The invention has been described in detail with particular reference to preferred embodiments thereof, but it will be understood that variations and modifications can be effected within the spirit and scope of the invention.

We claim:

1. A catalyst composition comprising:

a complex of cobalt, iodide, and an onium cation or an alkali metal cation of the general formula $Y_2CoI_4$, wherein Y is said onium cation or said alkali metal cation: and a phosphine ligand of the general formula

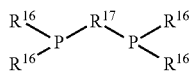

TABLE 9

Partitioning of components in the crude reductive carbonylation product

| Ex. | Co-solvent | MeOH Conv. | Yield of Carbonylated Products | Product Layer | Water | MeOH | AcH | $(MeO)_2Et$ | EtOH | HOAc | MeOAc | HBu |
|---|---|---|---|---|---|---|---|---|---|---|---|---|
| 84 | Toluene | 84% | 49% | Non-polar | 4% | 17% | 25% | 77% | 26% | 34% | 75% | 69% |
| | | | | Polar | 96% | 83% | 75% | 23% | 74% | 66% | 25% | 31% |
| 85 | Heptane | 80% | 41% | Non-polar | 2% | 4% | 5% | 51% | 7% | 12% | 34% | 22% |

TABLE 10

Partitioning of catalyst in the crude reductive carbonylation product

| Ex. | Co-solvent | Product Layer | Cobalt content (ppm) | Iodine content (ppm) | Phosphorus content (ppm) |
|---|---|---|---|---|---|
| 86 | Toluene | Non-polar (upper) | <10.0 | 1288 | 272 |
| | | Polar (lower) | 1564 | 45923 | 3623 |
| 87 | Heptane | Non-polar (upper) | <10.0 | 92 | <10.0 | wherein phosphorus atoms P are bridged by 2 to 6 atoms of $R^{17}$, wherein $R^{17}$ is selected from the group consisting of substituted or unsubstituted alkylene, cycloalkylene, arylene, and biarylene, each having up to 22 carbon atoms; wherein a heteroatom, optionally, can substitute for one or more of said carbon atoms, wherein said heteroatom is selected from the group consisting of nitrogen, oxygen, sulfur, and phosphorus; and $R^{16}$ is selected from the group consisting of substituted or unsubstituted alkyl, alkoxy, cycloalkyl, aryl, and aryloxy, each having up to 20 carbon atoms.

2. The catalyst composition according to claim 1, wherein said onium cation is of the general formula (I) or (II):

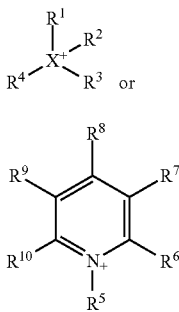

wherein X is selected from the group consisting of phosphorus (P) and nitrogen (N), $R^1$ is methyl, and $R^2$, $R^3$, and $R^4$ are independently selected from alkyl having up to 12 carbon atoms and aryl, wherein said aryl is selected from only one of the group consisting of phenyl, tolyl, xylyl, and mesityl; $R^5$ is methyl and $R^6$, $R^7$, $R^8$, $R^9$, and $R^{10}$ are hydrogen.

3. The catalyst composition according to claim 1, wherein said phosphine ligand is of the general formula

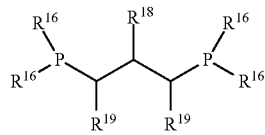

wherein $R^{18}$ is selected from the group consisting of a hydrogen radical and a hydrocarbon radical having up to 17 carbon atoms, wherein said hydrocarbon radical can be substituted with at least one substituent selected from the group consisting of alkyl, alkoxy, cycloalkyl, aryl, aryloxy, dialkylphosphinomethyl, and diarylphosphinomethyl; and $R^{19}$ is selected from the group consisting of hydrogen radical, and substituted or unsubstituted alkyl, alkoxy, cycloalkyl, aryl, and aryloxy, each having up to 8 carbon atoms.

4. The catalyst composition according to claim 3, wherein $R^{16}$ is selected from the group consisting of methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, and mesityl-oxy;

$R^{18}$ is selected from the group consisting of hydrogen radical, methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, mesityl-oxy, dimethylphosphinomethyl, diethylphosphinomethyl, di-n-propylphosphinomethyl, di-iso-propylphosphinomethyl, di-n-butylphosphinomethyl, di-iso-butylphosphinomethyl, di-tert-butylphosphinomethyl, dimethoxyphosphinomethyl, diethoxyphosphinomethyl, di-n-propoxyphosphinomethyl, di-iso-propoxyphosphinomethyl, di-n-butoxyphosphinomethyl, di-iso-butoxyphosphinomethyl, di-tert-butoxyphosphinomethyl, diphenylphosphinomethyl, ditolylphosphinomethyl, and dixylylphosphinomethyl; and $R^{19}$ is a hydrogen radical.

5. The catalyst composition according to claim 1, wherein said phosphine ligand is selected from the group consisting of 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1-tris(diphenylphosphinomethyl)ethane; 1,1,1-tris(diethylphosphinomethyl)ethane; 1,3-bis(dicyclohexylphosphino)propane; 1,3-bis(dimethylphosphino)propane; 1,3-bis(diisopropylphosphino)propane; 1,3-bis(di-tert-butylphosphino)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and 1,3-bis(diphenylphosphino)cyclobutane.

6. The catalyst composition according to claim 1, wherein said onium cation is selected from the group consisting of methyltriphenylphosphonium, methyltributylphosphonium, methyltrioctylphosphonium, and 1-methylpyridinium; wherein said phosphine ligand is selected from the group consisting of 1,3-bis(diphenylphosphino)propane, 1,1,1-tris(diphenylphosphinomethyl)ethane, and 1,1,1-tris(diethylphosphinomethyl)ethane; and wherein the molar ratio of said phosphine ligand to said cobalt (phosphine ligand: cobalt) ranges from 0.025:1 to 2:1.

7. A process for the preparation of a crude reductive carbonylation product comprising contacting hydrogen, carbon monoxide, and an alcohol having 1 to 3 carbon atoms in the presence of a catalyst composition to form said crude reductive carbonylation product comprising homologous aldehyde equivalents in a higher mole percent than homologous acid equivalents or homologous alcohol equivalents, each based on the total moles of said homologous aldehyde equivalents, said homologous acid equivalents, and said homologous alcohol equivalents:

wherein said catalyst composition comprises a complex of cobalt, iodide, and an onium cation or an alkali metal cation of the general formula $Y_2CoI_4$, wherein Y is said onium cation or said alkali metal cation and a phosphine ligand, wherein said phosphine ligand is of the general formula

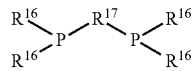

wherein phosphorus atoms P are bridged by 2 to 6 atoms of $R^{17}$, wherein $R^{17}$ is selected from the group consisting of substituted or unsubstituted alkylene, cycloalkylene, arylene, and biarylene, each having up to 22 carbon atoms; wherein a heteroatom, optionally, can substitute for one or more of said carbon atoms, wherein said heteroatom is selected from the group consisting of nitrogen, oxygen, sulfur, and phosphorus:

wherein $R^{16}$ is selected from the group consisting of substituted or unsubstituted alkyl, alkoxy, cycloalkyl, aryl, and aryloxy, each having up to 20 carbon atoms: and wherein said crude reductive carbonylation product comprises less than 1 weight percent of methyl iodide, based on the total weight of said crude reductive carbonylation product.

8. The process according to claim 7, wherein said onium cation is of the general formula (I) or (II):

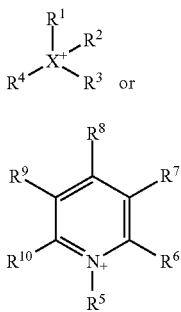

wherein X is selected from the group consisting of phosphorus (P) and nitrogen (N), $R^1$ is methyl, and $R^2$, $R^3$, and $R^4$ are independently selected from alkyl having up to 12 carbons and aryl, wherein said aryl is selected from only one of the group consisting of phenyl, tolyl, xylyl, and mesityl; $R^5$ is methyl and $R^6$, $R^7$, $R^8$, $R^9$, and $R^{10}$ are hydrogen.

9. The process according to claim 7, wherein said phosphine ligand is of the general formula

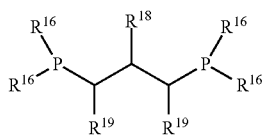

wherein $R^{18}$ is selected from the group consisting of a hydrogen radical and a hydrocarbon radical having up to 17 carbon atoms, wherein said hydrocarbon radical may be substituted with at least one substituent selected from the group consisting of alkyl, alkoxy, cycloalkyl aryl, aryloxy dialkylphosphinomethyl, and diarylphosphinomethyl; and $R^{19}$ is selected from the group consisting of a hydrogen radical, and a substituted or unsubstituted alkyl, alkoxy, cycloalkyl, aryl, and aryloxy, each having up to 8 carbon atoms.

10. The process according to claim 9, wherein $R^{16}$ is selected from the group consisting of methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, and mesityl-oxy;

$R^{18}$ is selected from the group consisting of hydrogen radical, methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, mesityl-oxy, dimethylphosphinomethyl, diethylphosphinomethyl, di-n-propylphosphinomethyl, di-iso-propylphosphinomethyl, di-n-butylphosphinomethyl, di-iso-butyl phosphinomethyl, di-tert-butylphosphinomethyl, dimethoxyphosphinomethyl, diethoxyphosphinomethyl, di-n-propoxyphosphinomethyl, di-iso-propoxyphosphinomethyl, di-n-butoxyphosphinomethyl, di-iso-butoxyphosphinomethyl, di-tert-butoxyphosphinomethyl, diphenylphosphinomethyl, ditolylphosphinomethyl, and dixylylphosphinomethyl; and $R^{19}$ is a hydrogen radical.

11. The process according to claim 7, wherein the phosphine ligand is selected from the group consisting of 1,2-bis(diphenylphosphino)ethane; 1,4-bis(diphenylphosphino) butane; 1,6-bis(diphenylphosphino)hexane; 1,2-bis (diphenylphosphino)benzene; bis (diphenylphosphinomethyl)biphenyl; 1,3-bis (diphenylphosphino)propane; 1,1,1-tris (diphenylphosphinomethyl)ethane; 1,1,1-tris (diethylphosphinomethyl)ethane; 1,3-bis (dicyclohexylphosphino)propane; 1,3-bis (dimethylphosphino)propane; 1,3-bis (diisopropylphosphino)propane; 1,3-bis(di-tert-butylphosphino)propane; (2-butoxy-2-((diphenylphosphino)methyl)propane-1,3-diyl)bis (diphenylphosphine); 1,8-bis(diphenylphosphino) naphthalene; bicyclo[2.2.1]heptane-2,7-diylbis (diphenylphosphine); 1,3-bis(diphenylphosphino) cyclohexane; 1,3-bis(diphenylphosphino)cyclopentane; and 1,3-bis(diphenylphosphino)cyclobutane.

12. The process according to claim 7, wherein said onium cation is selected from the group consisting of methyltriphenylphosphonium, methyltributylphosphonium, methyltrioctylphosphonium, and 1-methylpyridinium or said alkali metal cation is selected from the group consisting of lithium, sodium, potassium, rubidium, and cesium.

13. The process according to claim 7, wherein said onium cation is selected from the group consisting of methyltriphenylphosphonium, methyltributylphosphonium, methyltrioctylphosphonium, and 1-methylpyridinium and wherein said phosphine ligand is selected from the group consisting of 1,3-bis(diphenylphosphino)propane; 1,1,1-tris(diphenylphosphinomethyl)ethane; and 1,1,1-tris(diethylphosphinomethyl)ethane.

14. The process according to claim 7, wherein said cobalt is present in an amount ranging from 0.001 moles to 10 moles of said cobalt per 100 moles of said alcohol and wherein the mole ratio of said phosphine ligand to said cobalt (phosphine ligand:cobalt) ranges from 0.025:1 to 2:1.

15. The process according to claim 14, wherein said molar ratio of said phosphine ligand to said cobalt (phosphine ligand:cobalt) ranges from 0.1:1 to 1.5:1.

16. The process according to claim 7, wherein said process is carried out at a temperature ranging from 100° C. to 250° C. and at a pressure ranging from 100 kPa (15 psig) to 60 MPa (8700 psig), and wherein the molar ratio of said carbon monoxide to said hydrogen, $CO:H_2$, ranges from 10:1 to 1:10.

17. The process according to claim 7, wherein said contacting further occurs in the presence of a solvent selected the group consisting of alkanes and arenes having 6 to 20 carbon atoms, ketones having 5 to 20 carbon atoms, esters having 5 to 20 carbon atoms, ethers having 5 to 20 carbon atoms, and alky carbonate esters having 3 to 20 carbon atoms.

18. The process according to claim 7, wherein said alcohol comprises methanol, the $CO:H_2$ molar ratio ranges from 5:1 to 1:5, said process is carried out at a temperature ranging from 100° C. to 250° C. and a pressure ranging from 100 kPa (15 psig) to 60 MPa (8700 psig), and wherein said crude reductive carbonylation product comprises acetaldehyde equivalents in a higher mole percent than acetic acid equivalents or ethanol equivalents, each based on the total moles of acetaldehyde equivalents, acetic acid equivalents, and ethanol equivalents.

19. The process according to claim 7, wherein said alcohol comprises ethanol, the $CO:H_2$ molar ratio ranges from 5:1 to 1:5, said process is carried out at a temperature ranging from 100° C. to 250° C. and a pressure ranging from 100 kPa (15 psig) to 60 MPa (8700 psig) and wherein said crude reductive carbonylation product comprises n-propionaldehyde equivalents in a higher mole percent than n-propionic acid equivalents or n-propanol equivalents, each based on the total moles of n-propionaldehyde equivalents, n-propionic acid equivalents, and n-propanol equivalents.

20. The process according to claim 7, wherein said alcohol comprises n-propanol, the CO:H$_2$ molar ratio ranges from 5:1 to 1:5, said process is carried out at a temperature ranging from 100° C. to 250° C. and a pressure ranging from 100 kPa (15 psig) to 60 MPa (8700 psig), and wherein said crude reductive carbonylation product comprises n-butyraldehyde equivalents in a higher mole percent than n-butyric acid equivalents or n-butanol equivalents, each based on the total moles of n-butyraldehyde equivalents, n-butyric acid equivalents, and n-butanol equivalents.

21. A process for the preparation of a crude reductive carbonylation product comprising contacting hydrogen, carbon monoxide, and methanol in the presence of a catalyst composition to form said crude reductive carbonylation product, wherein said crude reductive carbonylation product comprises acetaldehyde equivalents in a higher mole percent than acetic acid equivalents or ethanol equivalents, each based on the total moles of acetaldehyde equivalents, acetic acid equivalents, and ethanol equivalents,
wherein said catalyst composition comprises a complex of cobalt, iodide, and an onium cation of the general formula Y$_2$CoI$_4$, wherein Y is said onium cation of the general formula (I) or (II)

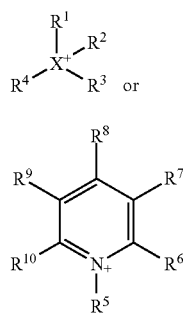

wherein X is phosphorus (P), R$^1$ is methyl, and R$^2$, R$^3$, and R$^4$ are independently selected from alkyl having up to 12 carbons and aryl wherein said aryl is selected from only one of the group consisting of phenyl, tolyl, xylyl, and mesityl; R$^5$ is methyl and R$^6$, R$^7$, R$^8$, R$^9$, and R$^{10}$ are hydrogen; and a phosphine ligand, wherein said phosphine ligand is selected from the group consisting of 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1-tris(diphenylphosphinomethyl)ethane; 1,1,1-tris(diethylphosphinomethyl)ethane; 1,3-bis(dicyclohexylphosphino)propane; 1,3-bis(dimethylphosphino)propane; 1,3-bis(diisopropylphosphino)propane; 1,3-bis(di-tert-butylphosphino)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and 1,3-bis(diphenylphosphino)cyclobutane; and
wherein said crude reductive carbonylation product comprises less than 1 weight percent of methyl iodide, based on the total weight of said crude reductive carbonylation product.

22. The process according to claim 21, wherein said phosphine ligand is selected from the group consisting of 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1-tris(diphenylphosphinomethyl)ethane; 1,1,1-tris(diethylphosphinomethyl)ethane.

23. The process according to claim 21, wherein said onium cation is selected from the group consisting of methyltriphenylphosphonium, methyltributylphosphonium, methyltrioctylphosphonium, and 1-methylpyridinium and wherein said phosphine ligand is selected from the group consisting of 1,3-bis(diphenylphosphino)propane; 1,1,1-tris(diphenylphosphinomethyl)ethane; and 1,1,1-tris(diethylphosphinomethyl)ethane.

24. The process according to claim 21, wherein said cobalt is present in an amount ranging from 0.02 moles to 5 moles of said cobalt per 100 moles of said methanol and wherein the mole ratio of said phosphine ligand to said cobalt (phosphine ligand:cobalt) ranges from 0.025:1 to 2:1.

25. The process according to claim 21, wherein the molar ratio of said carbon monoxide to said hydrogen, CO:H$_2$, ranges from 10:1 to 1:10.

26. The process according to claim 21, wherein said process is carried out at a temperature ranging from 150° C. to 230° C. and a pressure ranging from 1 MPa (150 psig) to 40 MPa (5800 psig).

27. The process according to claim 21, wherein said contacting further occurs in the presence of a solvent selected from the group consisting of toluene, heptane, cyclohexane, ethylbenzene, diethyl ether, and 4-methylanisole.

28. A process for the preparation of a crude reductive carbonylation product comprising contacting hydrogen, carbon monoxide, and an alcohol having 1 to 3 carbon atoms in the presence of a catalyst composition to form said crude reductive carbonylation product comprising homologous alcohol equivalents in a higher mole percent than homologous aldehyde equivalents or homologous acid equivalents, each based on the total moles of said homologous aldehyde equivalents, said homologous acid equivalents, and said homologous alcohol equivalents:
wherein said catalyst composition comprises a complex of cobalt, iodide, and an onium cation or an alkali metal cation of the general formula Y$_2$CoI$_4$, wherein Y is said onium cation or said alkali metal cation and a phosphine ligand, wherein said phosphine ligand is of the general formula

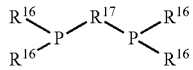

wherein phosphorus atoms P are bridged by 2 to 6 atoms of R$^{17}$, wherein R$^{17}$ is selected from the group consisting of substituted or unsubstituted alkylene, cycloalkylene, arylene, and biarylene, each having up to 20 carbon atoms; wherein a heteroatom, optionally, can substitute for one or more of said carbon atoms, wherein said heteroatom is selected from the group consisting of nitrogen, oxygen, sulfur, and phosphorus:
$R^{16}$ is selected from the group consisting of substituted or unsubstituted alkyl, alkoxy, cycloalkyl, aryl, and aryloxy, each having up to 20 carbon atoms: and
further comprising a ruthenium co-catalyst: and
wherein said crude reductive carbonylation product comprises less than 1 weight percent of methyl iodide, based on the total weight of said crude reductive carbonylation product.

29. The process according to claim 28, wherein said onium cation is of the general formula (I) or (II):

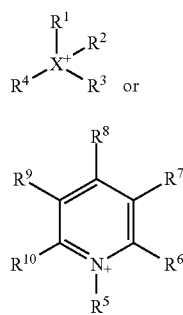

(I)

(II)

wherein X is selected from the group consisting of phosphorus (P) and nitrogen (N), $R^1$ is methyl, and $R^2$, $R^3$, and $R^4$ are independently selected from alkyl having up to 12 carbons and aryl, wherein said aryl is selected from only one of the group consisting of phenyl, tolyl, xylyl, and mesityl; $R^5$ is methyl and $R^6$, $R^7$, $R^8$, $R^9$, and $R^{10}$ are hydrogen.

30. The process according to claim 28, wherein said phosphine ligand is selected from the group consisting of 1,2-bis(diphenylphosphino)ethane; 1,4-bis(diphenylphosphino)butane; 1,6-bis(diphenylphosphino)hexane; 1,2-bis(diphenylphosphinomethyl)benzene; bis(diphenylphosphinomethyl)biphenyl; 1,3-bis(diphenylphosphino)propane; 1,1,1-tris(diphenylphosphinomethyl)ethane; 1,1,1-tris(diethylphosphinomethyl)ethane; 1,3-bis(dicyclohexylphosphino)propane; 1,3-bis(dimethylphosphino)propane; 1,3-bis(diisopropylphosphino)propane; 1,3-bis(di-tert-butylphosphino)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and 1,3-bis(diphenylphosphino)cyclobutane.

31. The process according to claim 28, wherein said complex is selected from the group consisting of bis(methyltriphenylphosphonium) cobalt tetraiodide, bis(methyltributylphosphonium) cobalt tetraiodide, bis(methyltrioctylphosphonium), and bis(1-methylpyridinium) cobalt tetraiodide,
wherein said phosphine ligand is selected from the group consisting of 1,3-bis(diphenylphosphino)propane; and 1,1,1-tris(diphenylphosphinomethyl)ethane; 1,1,1-tris(diethylphosphinomethyl)ethane,
wherein the $CO:H_2$ molar ratio ranges from 1:1 to 1:10, and
wherein said process is carried out at a temperature ranging from 150° C. to 230° C. and a pressure ranging from 6.9 MPa (1000 psig) to 34 MPA (4900 psig).

32. The process according to claim 28, wherein said alcohol comprises methanol, the $CO:H_2$ molar ratio ranges from 1:1 to 1:5, and said process is carried out at a temperature ranging from 100° C. to 250° C. and a pressure ranging from 100 kPa (15 psig) to 60 MPa (8700 psig), and wherein said crude reductive carbonylation product comprises ethanol equivalents in a higher mole percent than acetaldehyde equivalents or acetic acid equivalents, each based on the total moles of acetaldehyde equivalents, acetic acid equivalents, and ethanol equivalents.

33. The process according to claim 28, wherein said alcohol comprises ethanol, the $CO:H_2$ molar ratio ranges from 1:1 to 1:5, said process is carried out at a temperature ranging from 100° C. to 250° C. and a pressure ranging from 100 kPa (15 psig) to 60 MPa (8700 psig), and wherein said crude reductive carbonylation product comprises n-propanol equivalents in a higher mole percent than n-propionaldehyde equivalents or n-propionic acid equivalents, each based on the total moles of n-propionaldehyde equivalents, n-propionic acid equivalents, and n-propanol equivalents.

34. The process according to claim 28, wherein said alcohol comprises n-propanol, the CO:H2 molar ratio ranges from 1:1 to 5, said process is carried out at a temperature ranging from 100° C. to 250° C. and a pressure ranging from 100 kPa (15 psig) to 60 MPa (8700 psig) and wherein said crude reductive carbonylation product comprises n-butanol equivalents in a higher mole percent than n-butyraldehyde equivalents or n-butyric acid equivalents, each based on the total moles of n-butyraldehyde equivalents, n-butyric acid equivalents, and n-butanol equivalents.

* * * * *